United States Patent
Baker et al.

[11] Patent Number: 5,883,119
[45] Date of Patent: Mar. 16, 1999

[54] TRITERPENE DERIVATIVES WITH IMMUNOSUPPRESSANT ACTIVITY

[75] Inventors: Robert K. Baker, Cranford; Frank Kayser, Hoboken; Jianming Bao, Westfield; William H. Parsons, Belle Mead; Kathleen M. Rupprecht, Cranford, all of N.J.

[73] Assignee: Merck & Co., Inc., Rahway, N.J.

[21] Appl. No.: 733,032

[22] Filed: Oct. 16, 1996

Related U.S. Application Data

[60] Provisional application No. 60/008,190 Oct. 31, 1995 and provisional application No. 60/007,116 Oct. 31, 1995.

[51] Int. Cl.⁶ ..................... A61K 31/335; A61K 31/415; A61K 31/38
[52] U.S. Cl. .................. 514/450; 514/397; 514/444; 548/311.7; 549/60; 549/268; 549/354
[58] Field of Search ..................... 514/450, 444, 514/397; 549/268, 348, 60, 354; 548/311.7

[56] References Cited

U.S. PATENT DOCUMENTS 5,631,282  5/1997  Goetz ........................................ 514/450

FOREIGN PATENT DOCUMENTS

WO 96/40688  12/1996  WIPO.

OTHER PUBLICATIONS

Abreu, et al., "A Nor-Triterpenoid from Lophanthera Lactescens.", Phytochemistry, vol. 29(7), pp. 2257–2261, 1990.

*Primary Examiner*—Amelia Owens
*Attorney, Agent, or Firm*—J. Antonio Garcia-Rivas; Valerie J. Camara; Mark R. Daniel

[57] ABSTRACT

The compounds of Formula I

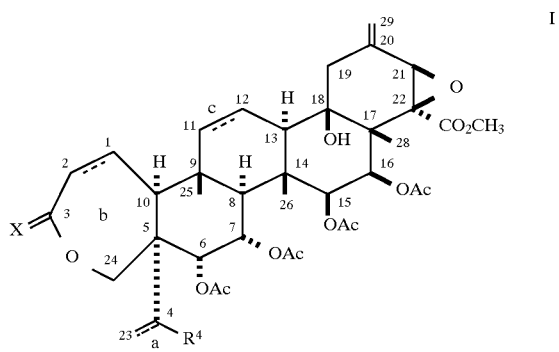

are useful as immunosuppressive agents.

15 Claims, No Drawings

TRITERPENE DERIVATIVES WITH IMMUNOSUPPRESSANT ACTIVITY

This application is related to provisional application 60/008,190 and 60/007,416 both filed Oct. 31, 1995.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort.

Newer, safer drugs exhibiting less side effects are constantly being searched for in the field.

Four active components of *Spachea correa* were recently identified which inhibit thymidine uptake of T cells and are useful as immunosuppressive agents in animals, including man.

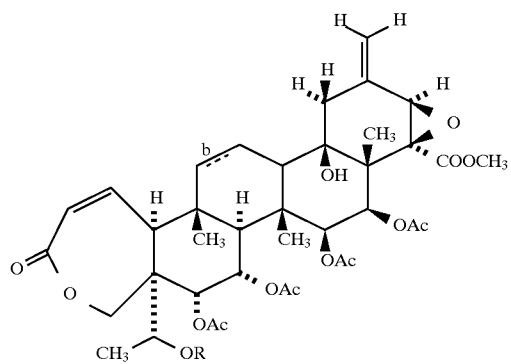

Formula 1(a) b is a single bond and R is OAc
Formula 1(b) b is a double bond and R is OAc
Formula 1(c) b is a single bond and R is OH
Formula 1(d) b is a double bond and R is OH These compounds are useful as immunosuppressive agents in animals, including man. The present invention describes newly developed immunosuppressive compounds derived from the compounds described in Formulae 1(a) through 1(d) and which have the relative stereochemistry depicted above.

SUMMARY OF THE INVENTION

This invention relates to a class of triterpene derivatives of the general structural Formula I

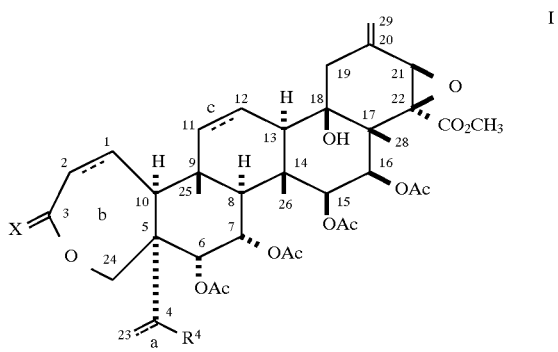

are useful as immunosuppressants.

As an immunosuppressant, the compounds of this invention are useful in the treatment of autoimmune diseases, the prevention of rejection of foreign organ transplants and/or related afflictions, diseases and illnesses. Also within the scope of this invention are pharmaceutical formulations comprising a compound of Formula I and a pharmaceutical carrier, as well as, pharmaceutical formulations comprising a compound of Formula I, a second immunosuppressant compound and a pharmaceutical carrier.

DETAILED DESCRIPTION OF THE INVENTION

A. Scope of the Invention

The present invention is related to compounds of formula I, including but not limited to those specified in the examples, which are useful in a mammalian subject for the treatment and prevention of the resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins), lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis sclerosing cholangitis), partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

More particularly, this invention relates to compounds of the general structural Formula I:

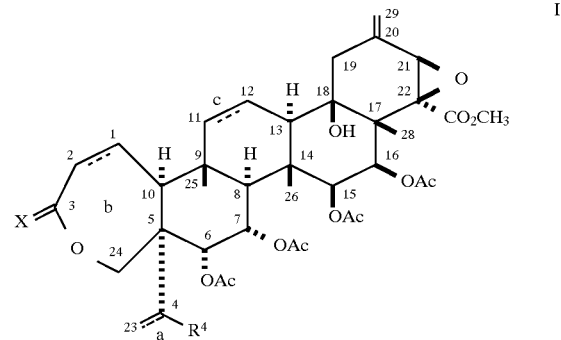

or a pharmaceutically acceptable salt, crystal form or hydrate, wherein:

X is: O, S, NH, H and $R^1$;

a is: a single bond, or a double bond when $R^4$ is absent;

b and c are independently: a single bond or a double bond;

n is: 1 to 4;

m is: 1 to 4;

r is: 0 or 1;

s is: 0 or 1;

$R^1$ and $R^2$ are independently:
  a) H, or
  b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
  a) $-(C_1-C_6)$-alkyl, alkyl as defined above;
  b) $-(C_1-C_6)$-alkenyl, wherein alkenyl is unsubstituted or substituted with one, two or three substituents selected from from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above;
c) -$(C_1-C_6)$-alkynyl, wherein alkynyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above,
d) -aryl, aryl as defined above, or
e) -heteroaryl, heteroaryl as defined above;

$R^4$ is:
a) absent and a is a double bond;
b) —H,
c) —OH,
d) =O,
e) —O[(C=O)O$_r$]$_s$C$_1$–C$_{10}$-alkyl, alkyl as defined above,
f) —O[(C=O)O$_r$]$_s$C$_2$–C$_{10}$-alkenyl, as defined above,
g) —O[(C=O)O$_r$]$_s$C$_2$–C$_6$-alkynyl, alkynyl as defined above,
h) —O[(C=O)O$_r$]$_s$(C$_3$–C$_7$)-cycloalkyl,
i) —O[(C=O)O$_r$]$_s$aryl, aryl as defined above,
j) —O[(C=O)O$_r$]$_s$heteroaryl heteroaryl as defined above,
k) —O(CH$_2$)$_n$O(CH$_2$)$_m$heteroaryl, heteroaryl as defined above,
l) —O(CH$_2$)$_n$O(CH$_2$)$_m$aryl, aryl as defined above,
m) —OC(=O)NR$^1$R$^2$,
n) —OSO$_2$R$^3$,
o) —NR$^1$R$^2$; or
p) (C$_2$–C$_6$)-alkenyl, alkenyl as described above.

An embodiment of the invention are the compounds of Formula I or a pharmaceutically acceptable salt, crystal form or hydrate, wherein:
X is: O, S, or NH;
a is: a single bond;
b and c are independently: a single bond or a double bond;
n is: 1 to 4;
m is: 1 to 4;
r is: 0 or 1;
s is: 0 or 1;
$R^1$ and $R^2$ are independently:
a) H, or
b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2-C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) -$(C_1-C_6)$-alkyl, alkyl as defined above;
b) -$(C_1-C_6)$-alkenyl, wherein alkenyl is unsubstituted or substituted with one, two or three substituents selected from from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above;
c) -$(C_1-C_6)$-alkynyl, wherein alkynyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above,
d) -aryl, aryl as defined above, or
e) -heteroaryl, heteroaryl as defined above;

$R^4$ is:
a) absent and a is a double bond;
b) —H,
c) —OH,
d) =O,
e) —O[(C=O)O$_r$]$_s$C$_1$–C$_{10}$-alkyl, alkyl as defined above,
f) —O[(C=O)O$_r$]$_s$C$_2$–C$_{10}$-alkenyl, as defined above,
g) —O[(C=O)O$_r$]$_s$C$_2$–C$_6$-alkynyl, alkynyl as defined above,
h) —O[(C=O)O$_r$]$_s$(C$_3$–C$_7$)-cycloalkyl,
i) —O[(C=O)O$_r$]$_s$aryl, aryl as defined above,
j) —O[(C=O)O$_r$]$_s$heteroaryl, heteroaryl as defined above,
k) —O(CH$_2$)$_n$O(CH$_2$)$_m$heteroaryl, heteroaryl as defined above,
l) —O(CH$_2$)$_n$O(CH$_2$)$_m$aryl, aryl as defined above,
m) —OC(=O)NR$^1$R$^2$,
n) —OSO$_2$R$^3$,
o) —NR$^1$R$^2$; or
p) (C$_2$–C$_6$)-alkenyl, alkenyl as described above.

An embodiment of this embodiment of the invention are the compounds of Formula I

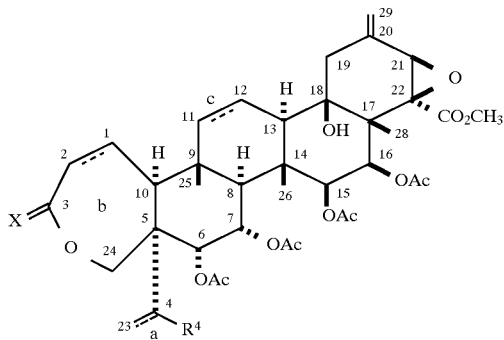

or a pharmaceutically acceptable salt, crystal form or hydrate, wherein:

X is: O;

a is: a single bond;

b and c are independently: single bond or a double bond;

n is: 1 to 4;

m is: 1 to 4;

r is: 0 or 1;

s is: 0 or 1;

$R^1$ and $R^2$ are independently:
  a) H, or
  b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
  a) —$(C_1-C_6)$-alkyl, alkyl as defined above,
  b) -aryl, aryl as defined above, or
  c) -heteroaryl, heteroaryl as defined above;

$R^4$ is:
  a) —O[(C=O)O$_r$]$_s$$C_1-C_{10}$-alkyl, alkyl as defined above,
  b) —O[(C=O)O$_r$]$_s$$(C_3-C_7)$-cycloalkyl,
  c) —O[(C=O)O$_r$]$_s$aryl, aryl as defined above,
  d) —O[(C=O)O$_r$]$_s$heteroaryl, heteroaryl as defined above,
  e) —$O(CH_2)_nO(CH_2)_m$heteroaryl, heteroaryl as defined above,
  f) —$O(CH_2)_nO(CH_2)_m$aryl, aryl as defined above,
  g) —OC(=O)$NR^1R^2$, or
  h) —$OSO_2R_3$.

An embodiment of this embodiment are the compound of structural Formula I or a pharmaceutically acceptable salt, crystal form or hydrate, wherein:

$R^4$ is:
  a) —O[(C=O)O$_r$]$_s$aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, or
  b) —O[(C=O)O$_r$]$_s$heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6-or 7-membered fused ring said ring containing 1 or 2 oxygen atoms and the remainder carbon atoms, or any two adjacent substituents can be joined together to form a benzo-fused ring.

An embodiment of the invention are the compounds of Formula I

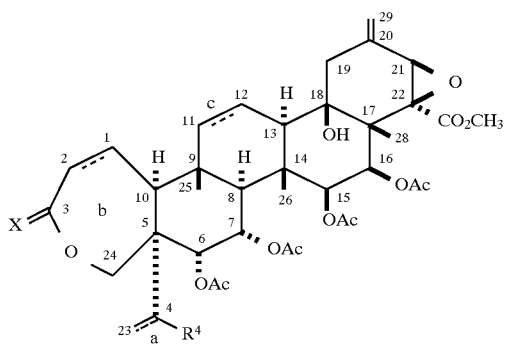

or a pharmaceutically acceptable salt, crystal form or hydrate, wherein:

X is: H and $R^1$;

a is: a single bond;

b and c are independently: a single bond or a double bond;

n is: 1 to 4;

m is: 1 to 4;

r is: 0 or 1;

s is: 0 or 1;

$R^1$ and $R^2$ are independently:
  a) H, or
  b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1–C_6$-alkyl, aryl, wherein aryl is defined as phenyl or naphthyl, unsubstituted or substituted with one, two or three substituents selected from the group consisting of: Br, Cl, F, I, ($C_1–C_6$)-alkoxy, phenyl, phenoxy, cyano, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1–C_6$)-alkoxy, cyano, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —($C_1–C_6$)-alkyl, alkyl as defined above;
b) —($C_1–C_6$)-alkenyl, wherein alkenyl is unsubstituted or substituted with one, two or three substituents selected from the group consisting of: Br, Cl, F, I, ($C_1–C_6$)-alkoxy, cyano, oxo, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl, aryl as defined above, and heteroaryl as defined above;
c) —($C_1–C_6$)-alkynyl, wherein alkynyl is unsubstituted or substituted with one, two or three substituents selected from the group consisting of: Br, Cl, F, I, ($C_1–C_6$)-alkoxy, cyano, oxo, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl, aryl as defined above, and heteroaryl as defined above,
d) -aryl, aryl as defined above, or
e) -heteroaryl, heteroaryl as defined above;

$R^4$ is:
a) absent and a is a double bond;
b) —H,
c) —OH,
d) =O,
e) —O[(C=O)$O_r$]$_s C_1–C_{10}$-alkyl, alkyl as defined above,
f) —O[(C=O)$O_r$]$_s C_2–C_{10}$-alkenyl, as defined above,
g) —O[(C=O)$O_r$]$_s C_2–C_6$-alkynyl, alkynyl as defined above,
h) —O[(C=O)$O_r$]$_s$($C_3–C_7$)-cycloalkyl,
i) —O[(C=O)$O_r$]$_s$aryl, aryl as defined above,
j) —O($CH_2$)$_n$O($CH_2$)$_m$heteroaryl, heteroaryl as defined above,
k) —O($CH_2$)$_n$O($CH_2$)$_m$heteroaryl, heteroaryl as defined above,
l) —O($CH_2$)$_n$O($CH_2$)$_m$aryl, aryl as defined above,
m) —OC(=O)$NR^1 R^2$,
n) —$OSO_2R^3$, or
o) —$NR^1R^2$.

An embodiment of this embodiment of the invention are the compounds of Formula I

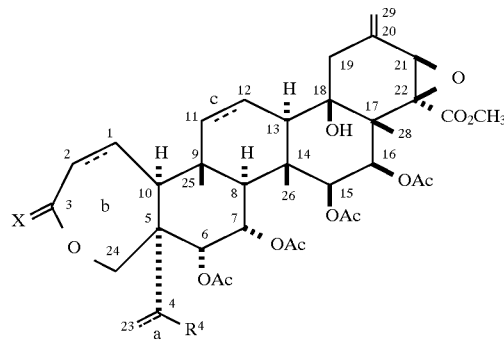

or a pharmaceutically acceptable salt, crystal form or hydrate, wherein:

X is: H and $R^1$;
a is: a single bond;
b is: a single bond or a double bond;
n is: 1 to 4;
m is: 1 to 4;
r is: 0 or 1;
s is: 0 or 1;
$R^1$ and $R^2$ are independently:
a) H, or
b) ($C_1–C_6$)-alkyl, wherein alkyl is unsubstituted or substituted with one, two or three substituents selected from the group consisting of: Br, Cl, F, I, ($C_1–C_6$)-alkoxy, vinyl, cyano, oxo, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl, aryl, wherein aryl is defined as phenyl or naphthyl, unsubstituted or substituted with one, two or three substituents selected from the group consisting of: Br, Cl, F, I, ($C_1–C_6$)-alkoxy, phenyl, phenoxy, cyano, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1–C_6$)-alkoxy, cyano, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —($C_1–C_6$)-alkyl, alkyl as defined above;
b) —($C_1–C_6$)-alkenyl, wherein alkenyl is unsubstituted or substituted with one, two or three substituents selected from the group consisting of: Br, Cl, F, I, ($C_1–C_6$)-alkoxy, cyano, oxo, nitro, hydroxy, CHO, $CO_2H$, $COC_1–C_6$-alkyl, $CO_2C_1–C_6$-alkyl, $CONR^1R^2$, $NR^1R^2$, $NR^1COC_1–C_6$-alkyl, aryl as defined above, and heteroaryl as defined above;
c) —($C_1–C_6$)-alkynyl, wherein alkynyl is unsubstituted or substituted with one, two or three substituents selected from the group consisting of: Br, Cl, F, I, ($C_1–C_6$)-alkoxy, cyano, oxo, nitro, hydroxy, CHO, $CO_2H$, $COC_1–C_6$-alkyl, $CO_2C_1–C_6$-alkyl, CONR$^1$R$^2$, NR$^1$R$^2$, NR$^1$COC$_1$–C$_6$-alkyl, aryl as defined above, and heteroaryl as defined above,
d) -aryl, aryl as defined above, or
e) -heteroaryl, heteroaryl as defined above;

R$^4$ is:
a) —OH,
b) —O[(C=O)O$_r$]$_s$C$_1$–C$_{10}$-alkyl, alkyl as defined above,
c) —O[(C=O)O$_r$]$_s$(C$_3$–C$_7$)-cycloalkyl,
d) —O[(C=O)O$_r$]$_s$aryl, aryl as defined above,
e) —O[(C=O)O$_r$]$_s$heteroaryl, heteroaryl as defined above,
f) —O(CH$_2$)$_n$O(CH$_2$)$_m$heteroaryl, heteroaryl as defined above,
g) —O(CH$_2$)$_n$O(CH$_2$)$_m$aryl, aryl as defined above,
h) —OC(=O)NR$^1$R$^2$, or
i) —OSO$_2$R$^3$.

An embodiment of the invention is a compound selected from the group consisting of:

6,7,15,16-tetrakis(acetyloxy)-21,22-epoxy-4,18-dihydroxy-22-methoxycarbonyl [6α,7α,15β,16β,21β,22β]D:A-Friedo-A-homo-27,30-dinor -24-oxaoleana-1,20(29)-dien-3-one;

4-benzoyloxy-6,7,15,16-tetrakis(acetyloxy)-21,22-epoxy-18-hydroxy-22-methoxycarbonyl [6α,7α,15β,16β,21β,22β]D:A-Friedo-A-homo-27,30-dinor-24-oxaoleana-1,20(29)-dien-3-one;

4-(2-chlorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one; 4-(4-methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-methoxyacetyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-chloroacetyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-bromobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-cyanobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(propanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2,2-dimethylpropanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(cyclohexylcarbonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-nitrobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(3-methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-bromobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2,3-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(3-methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(1-naphthoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-naphthoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-iodobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-trifluoromethylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(pentanoyl)oxy-6,7,15,16-tetrakis(acetyloxy)-21,22-epoxy-18-hydroxy-22-methoxycarbonyl[6α,7α,15β,16β,21β,22β]D:A-Friedo-A-15 homo-27,30-dinor-24-oxaoleana-1,20(29)-dien-3-one;

4-(2-fluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-furoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(benzyloxycarbonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(benzyloxymethyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-methanesulfonyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-methylbenzenesulfonyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(phenylmethanesulfonyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-chlorobenzenesulfonyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-methoxybenzenesulfonyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-butanesulfonyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-nitrobenzenesulfonyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-thiophenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(1-imidazolylcarbamoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(N-phenylmethylcarbamoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(N-butylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29) -dien-3-one;

4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4,6,7,15,16-pentakis(acetyloxy)-3-(2-propenyl)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;

4-(2-bromobenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;

4-(2-chlorobenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;

4-(2-iodobenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;

4-(2-methoxybenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;

4-(2-thienoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(3-bromobenzoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2-ethoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(4-phenylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2-phenoxybenzoyl)oxy-6,7,15,16-tetrakis(acetyloxy)-21,22-epoxy-18-hydroxy-22-methoxycarbonyl[6α,7α,15β,16β,21β,22β]D A-Friedo-A-homo-27,30-dinor-24-oxaoleana-1,20(29)-diene;

4-(3-phenoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2,4-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2,6-dichlorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2,6-dimethoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2,6-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2-acetyloxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2-[R]-2-phenylpropanoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(2-[S]-2-phenylpropanoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4-(3,5-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;

4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;

4,6,7,15,16-pentakis(acetyloxy)-21,22-epoxy-18-hydroxy-22-methoxycarbonyl[6α,7α,15β,16β, 21β,22β]D:A-Friedo-A-homo-27,30-dinor-24-oxaoleana-20(29)-ene;

4,6,7,15,16-pentakis(acetyloxy)-3-(2-propenyl)-21,22-epoxy-18-hydroxy-22-methoxycarbonyl[3α,6α,7α,15β,16β,21β,22β]D:A-Friedo-A-homo-27,30-dinor-24-oxaoleana-20(29)-ene;

4,6,7,15,16-pentakis(acetyloxy)-3-(2-propenyl)-21,22-epoxy-18-hydroxy-22-methoxycarbonyl[3β,6α,7α,15β,16β,21β,22β]D:A-Friedo-A-homo-27,30-dinor-24-oxaoleana-20(29)-ene;

6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-en-3-one;

6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-ene;

4-benzoyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;

4-(1-imidazolylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;

4-(N-phenylmethylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;

4-(N-butylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched- configuration and at least one unsaturation, which may occur at any point along the chain, such as ethenyl, propenyl, butenyl, pentenyl, dimethyl pentenyl, and the like, and includes E and Z forms, where applicable. "Halogen", as used herein, means fluoro, chloro, bromo and iodo.

The term "aryl" is defined as a phenyl or naphthyl ring which is optionally substituted at any available carbon atoms with one, two or three substituents selected from the group consisting of: Br, Cl, F, I, ($C_1$–$C_6$)-alkoxy, phenyl, phenoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein is intended to include the following a 5 or 6-membered ring substituted with one or two heteroatoms selected from O, S, N, and is unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl group may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens selected from the, the remaining ring atoms being carbon, selected from the group consisting of: dioxolanyl, dihydrofuranyl, dihydropyranyl, and dioxanyl.

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

REACTION SCHEME A

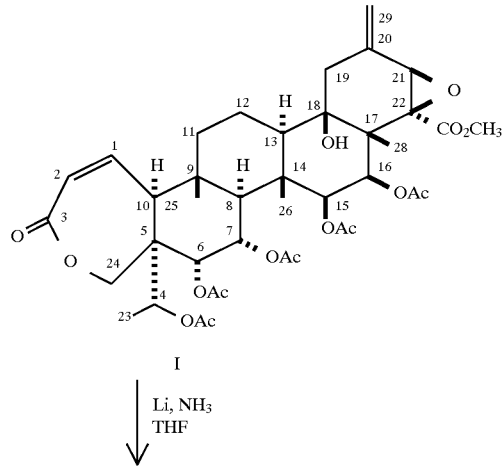

-continued
REACTION SCHEME A

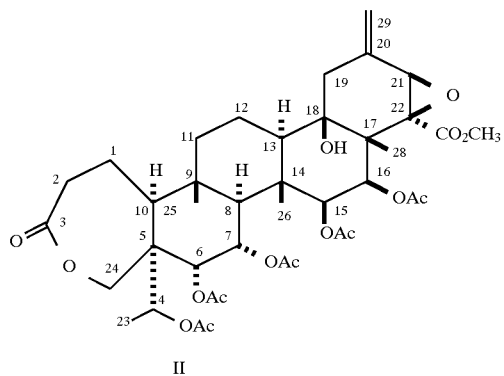

II

-continued
REACTION SCHEME B

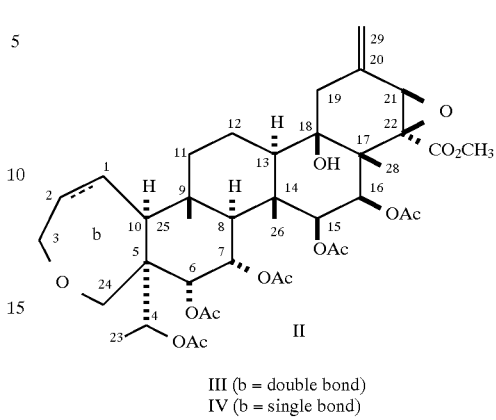

III (b = double bond)
IV (b = single bond)

As seen in Scheme A, compound I, 4,5,6,15,16-pentakis(acetyloxy)-21,22-epoxy-18-hydroxy-22-methoxycarbonyl[6α,7α, 15β,16β,21β,22β]D:A-Freido-A-homo-27,30-dinor-24-oxaoleana-1,20(29)-diene-3-one, isolated from *Spachea correa* in liquid ammonia with lithium metal will result in the reduction of the C1 olefin group to produce the saturated lactone. Alternative methods for reducing the C1 olefin group and/or the C20(29) olefin that are known in the art may also be employed. U.S. Ser. No. 08/476,806 filed on Jun. 7, 1995 describes the isolation of compound I and is hereby incorporated by reference. The resultant lactone can then be converted to the oxepin analog by procedures described in Reaction Scheme B.

It should also be noted that compounds of Formula I having the 11,12-double bond can be prepared using the starting material, 4,6,7,15,16-pentakisacetoxy-21,22-epoxy-18-hydroxy-22-methoxycarbonyl[6α,7α,15β,16β,21β,22β]D:A-Freido-A-homo-27,30-dinor-24-oxaleana-1,11,20(29)-trien-3-one, isolated from *Spachea correa* and following the procedures described herein. However, there may be reactions where it will not be possible to selectively operate on one of the double bonds, for example, ozonolysis.

As seen in Scheme B, compound I, [(4,6,7,15,16-pentakis(acetyloxy)-21,22-epoxy-18-hydroxy-22-methyoxycarbonyl-[6α,7α,15β,16β,21β,22β]D:A-Freido-A-homo-27,30-dinor-24-oxaoleana-1,20(29)-dien-3-one] isolated from *Spachea correa* or the product of Scheme A, II, can be converted to its oxepin analogs, III and IV, in a two step process. U.S. Ser. No. 08/476,806 filed on Jun. 7, 1995 describing the isolation of compound I and is hereby incorporated by reference. The resultant lactone can then be converted to the oxepin analogs by procedures described in Reaction Scheme B. Lactone I is first reduced to the lactol, which can be accomplished by using a variety of reducing agents including diisobutylaluminum hydride (DIBAL-H) and sodium bis(2-methoxyethoxy)aluminum hydride (Red-Al). A more optimal reducing agent is the use of lithium tri-t-butoxyaluminum hydride in an inert solvent such as dichloromethane at reduced temperatures, preferably 0° C. The purified lactol intermediate is then reacted with triethylsilane and a Lewis acid such as borontrifluoride diethyl etherate to give the ether (oxepin) analog of I.

REACTION SCHEME B

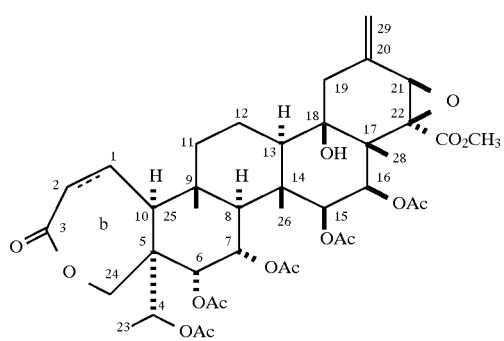

I (b = double bond)
II (b = single bond)

1. LiAlH(OtBu)₃
2. Et₃SiH, BF₃OEt₂

REACTION SCHEME C

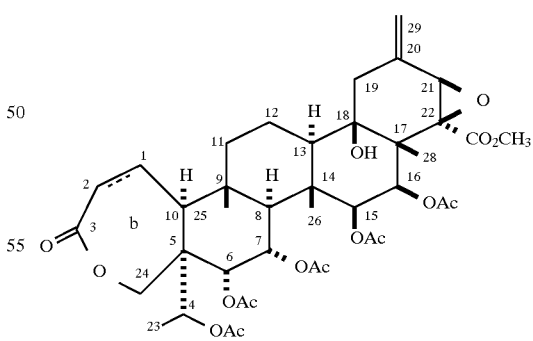

I (b = double bond)
II (b = single bond)

1. LiAlH(OtBu)₃
2. Et₃Al

REACTION SCHEME C

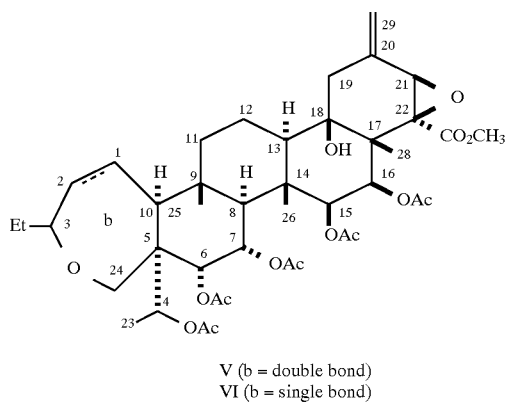

V (b = double bond)
VI (b = single bond)

In a variation of Scheme B, oxepin derivatives substituted at C3 can also be prepared. Thus in Reaction Scheme C, lactones I or II is first reduced to the lactol as described in Reaction Scheme B. The purified lactol intermediate is then reacted with a trialkylaluminum reagent, as exemplified in this scheme by triethylaluminum (Et$_3$Al) to give the ethyl derivative. The allyl derivative can be prepared with allyltrimethylsilane and a Lewis acid such as borontrifluoride diethyl etherate.

REACTION SCHEME D

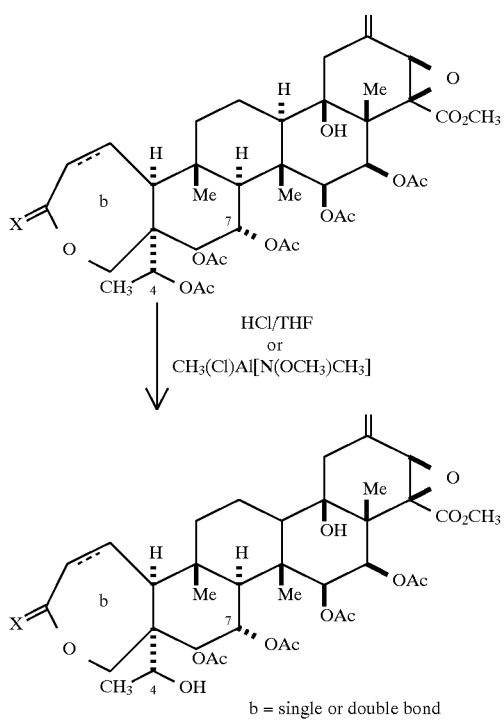

b = single or double bond

The C4 acetate (Scheme D) can be selectively de-acetylated to give the corresponding alcohol by reacting it with an aqueous solution of HCl (preferably 2M to 3M concentration) in THF. It can also be prepared by reaction with CH$_3$(Cl)Al[N(OCH$_3$)CH$_3$] (Weinreb reagent) in inert solvents such as THF, toluene or methylene chloride.

REACTION SCHEME E

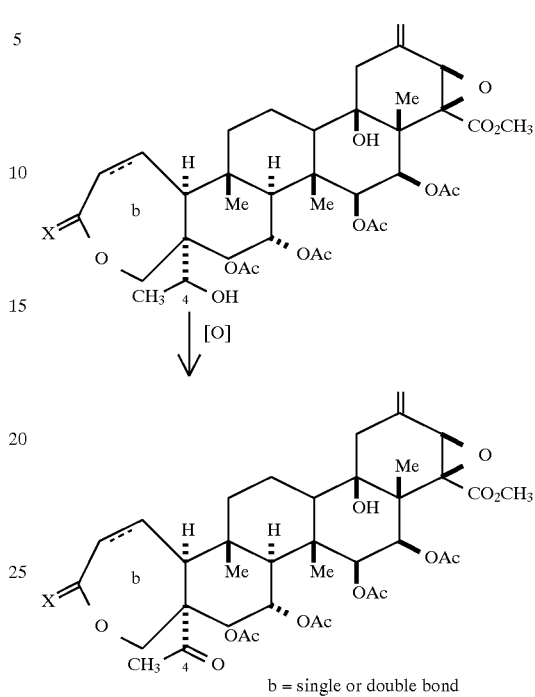

b = single or double bond

The C4 hydroxy group in Scheme E can be oxidized to the corresponding ketone by a variety of oxidizing agents. The Jones reagent (chromic acid and sulfuric acid in H$_2$O), pyridinium chlorochromate, and oxalyl chloride plus DMSO all will achieve this conversion.

REACTION SCHEME F

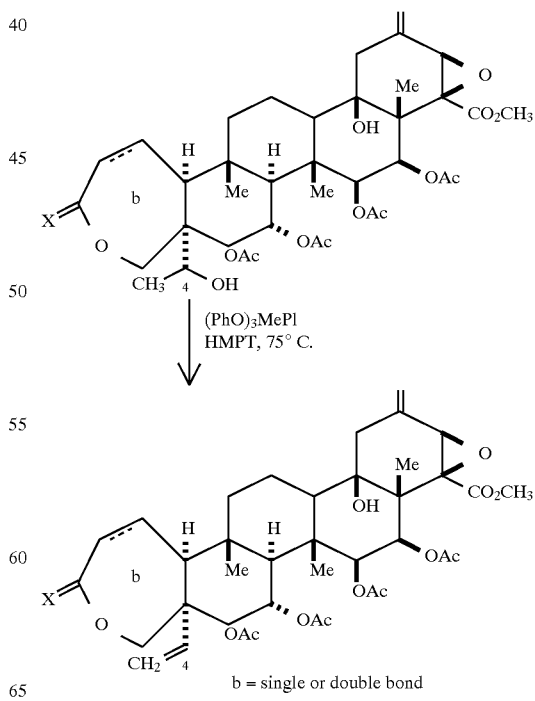

b = single or double bond

The C4 hydroxy group in Scheme F can also be dehydrated to give the olefin. Reaction of the alcohol with tris-phenoxymethylphos-phonium iodide in hexamethylphosphorous triamide (HMPT) at 75° C. will achieve this conversion.
REACTION SCHEME G
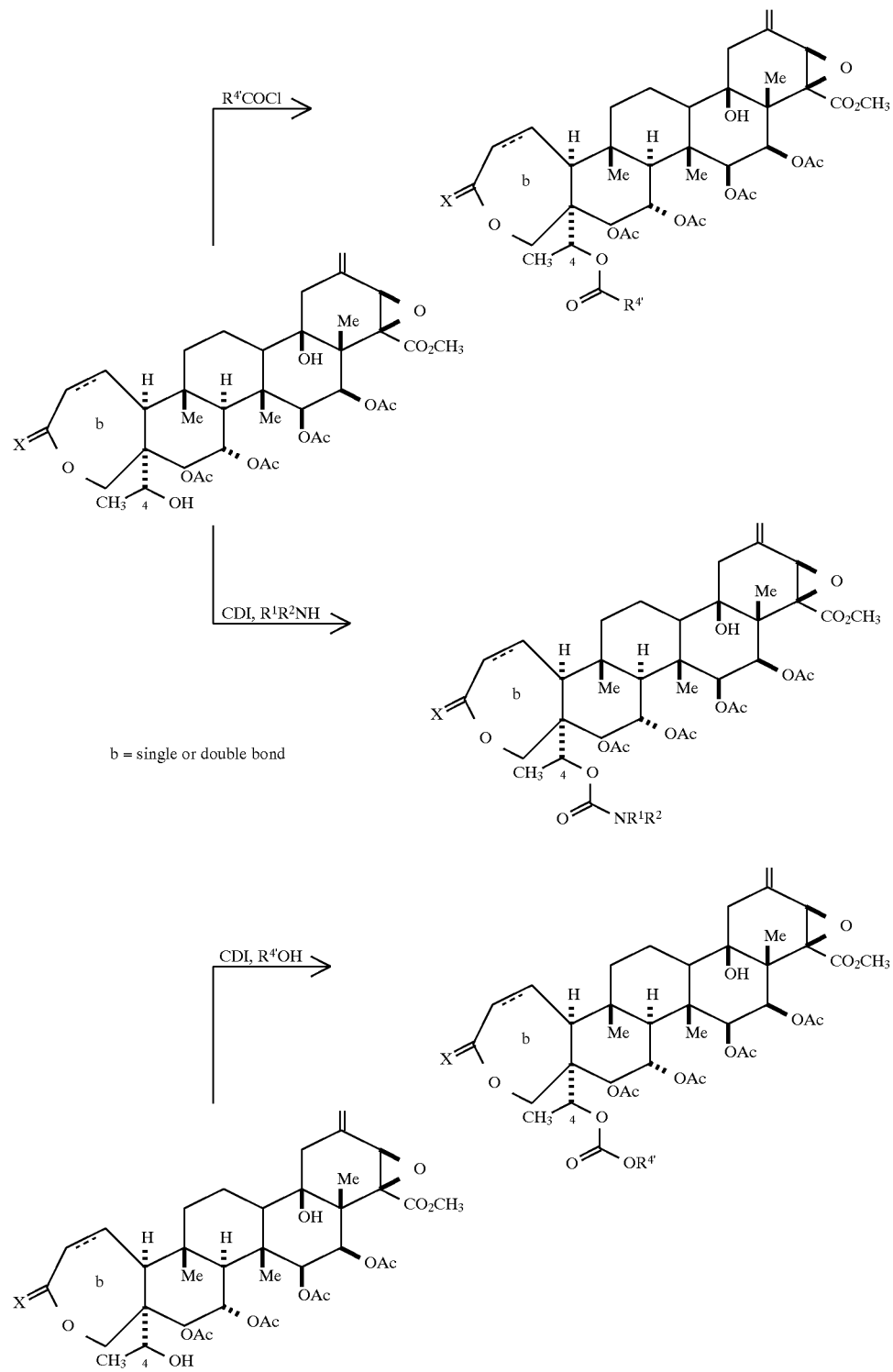
b = single or double bond

-continued
REACTION SCHEME G

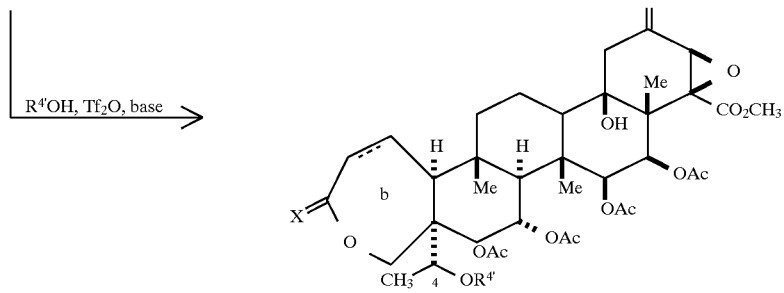

As depicted in Reaction Scheme G, esters at C4 can be prepared by reaction of a pre-formed carboxylic acid chloride with the C4 alcohol derivative (Reaction Scheme D) in a basic solvent such as pyridine. It should be understood that $R^{4'}$ is used to represent a portion of the $R^4$ definition, e.g. $R^4$ can be an alkyl carbonate which is depicted in the scheme as $OC(=O)OR^{4'}$, $R^{4'}$ representing the alkyl substituent. The acid chlorides, when not purchased, are prepared by stirring the carboxylic acids in reagents such as oxalyl chloride or thionyl chloride. Esters may also be prepared by reaction of the acid chloride and C4 alcohol with silver cyanide (AgCN) in an aprotic solvent such as HMPA. C4 sulfonate derivatives are prepared in a similar manner by reaction with sulfonyl chlorides.

C4 carbonate and carbamate derivatives are prepared by first reacting the C4 alcohol derivative with carbonyldiimidazole (CDI) to obtain the imidazolecarbonyl intermediate which is then reacted with an alcohol or amine ($R^1R^2NH$) to give the corresponding carbonate or carbamate derivatives.

C4 ether derivatives can also be prepared. The best procedure involves reacting an alcohol with trifluoromethanesulfonic anhydride ($Tf_2O$, triflic anhydride) to obtain the preformed triflate in dichloromethane at reduced temperature, preferably $-78°$ C. To this solution is added the triterpene alcohol, the reaction misture is warmed to room temperature and stirring is continued until reaction is complete. Ethers may also be prepared by heating a mixture of triterpene C4 alcohol, the appropriate alkylhalide and an excess of silver oxide ($Ag_2O$) in an aprotic invert solvent such as THF.

REACTION SCHEME H

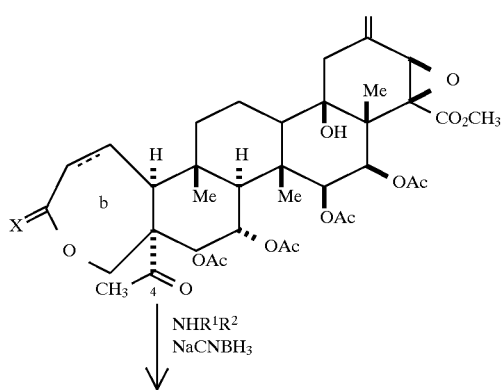

-continued
REACTION SCHEME H

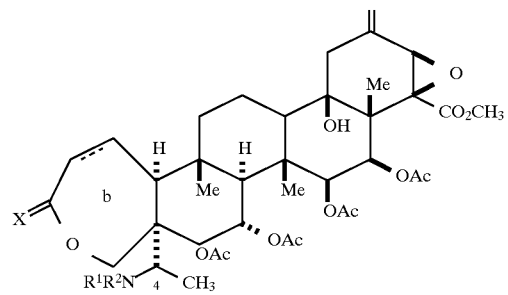

Amines at C4 (Scheme H) can be prepared from the C4 ketone described in Reaction Scheme E by reaction with an amine $NHR^1R^2$ in a variety of solvents with a reducing agent such as sodium cyanoborohydride.

UTILITY

The present invention is related to compounds of formula I, including but not limited to those specified in the examples, which are useful in a mammalian subject for the treatment and prevention of immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves opthalmopathy, Vogt- Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

A method of treating a condition in a mammal, the treatment of which is effected or facilitated by $K_v1.3$ inhibition, comprising the administration, in an amount that is effective at inhibiting $K_v1.3$, of a compound of Formula I. The method of treating a condition in a mammal, the treatment of which is effected or facilitated by $K_v1.3$ inhibition, wherein the condition is selected from the group consisting of: immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythiroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern aleopreia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali bum; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and immunodepression or a disorder involving immunodepression, such as AIDS, cancer, senile dementia, trauma (including wound healing, surgery and shock), chronic bacterial infection, and certain central nervous system disorders.

An embodiment of the invention is a method for the treatment of autoimmune diseases. Another embodiment of the invention is a method for the prevention of rejection of foreign organ transplants comprising administering to a patient in need of such treatment a therapeutically effective amount of a compound of formula I.

One end result of an autoimmune or a rejection process is tissue destruction caused by inflammatory cells and the mediators they release. Anti-inflammatory agents such as NSAID's and corticosteroids act principally by blocking the effect or secretion of these mediators, but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immuno-suppressive agents are as likely to succumb from infection as they are from their autoimmune disease.

Cyclosporin A, which was approved by the US FDA in 1983, is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting fewer side effects are constantly being searched for in the field. The present invention provides for immunosuppressant agents which are inhibitors of a voltage dependent potassium channel, $K_v1.3$, that is found on human T-lymphocytes.

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of $K^+$ channels, in their role as modulators of the plasma membrane potential in human T-lymphocytes, has been postulated to play a role in eliciting immunosuppressive responses. In regulating membrane potential, $K^+$ channels play a role in the regulation of intracellular $Ca^{++}$ homeostasis, which has been found to be important in T-cell activation. The biochemical characterization of $K^+$ channels is underdeveloped, due to the paucity of selective high affinity probes.

Functional voltage-gated $K^+$ channels can exist as multimeric structures formed by the association of either identical or dissimilar subunits. This phenomena is thought to account for the wide diversity of $K^{30}$ channels. However, subunit compositions of native $K^+$ channels and the physiologic role that particular channels play are, in most cases, still unclear.

The $K_v1.3$ channel is a voltage-gated potassium channel that is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., *J. Exp. Med.* 160, 369, 1984; Decoursey et al., *Nature,* 307, 465, 1984). However, the K+ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., *Proc. Natl. Acad. Sci. USA,* 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., *Proc. Natl. Acad. Sci. USA,* 89, 10094, 1992). Margatoxin, on the other hand, blocks only $K_v1.3$ in T-cells, and has immunosuppressant activity in both in vitro and in vivo models. (Lin et al., *J. Exp. Med,* 177, 637, 1993). Since the compounds of the embodiments of this invention produce blockade of $K_v1.3$, they will also inhibit T-cell activation.

Also within the scope of this invention is a method of treating a condition in a mammal, the treatment of which is effected or facilitated by $K_v1.3$ inhibition, comprising the administration of a pharmaceutical composition comprising a suitable pharmaceutical carrier and a compound of Formula (I), in an amount that is effective at inhibiting $K_v1.3$.

Also within the scope of this invention is a combination therapy comprising a compound of formula I and one or more immunosuppressant agents. These immunosuppressant agents within the scope of this invention include, but are not limited to, IMUREK® azathioprine sodium, brequinar sodium, SPANIDIN® gusperirnus trihydrochloride (also known as deoxyspergualin), mizoribine (also known as bredinin), CELLCEPT® mycophenolate mofetil, NEORAL® Cyclosporin A (also marketed as different formulation of Cyclosporin A under the trademark SANDIMMUNE®), PROGRAF® tacrolimus (also known as FK-506) and RAPIMMUNE® sirolimus (also known as rapamycin), leflunomide (also known as HWA-486), glucocortcoids, such as prednisolone and its derivatives, antibody therapies such as orthoclone (OKT3) and Zenapax and antithymyocyte globulins, such as thymoglobulins.

Using the methodologies described below, representative compounds of the invention were evaluated and found to exhibit IC50 values of at least <10 $\mu$M in any of the assays thereby demonstrating and confirming the utility of the compounds of the invention as $K_v1.3$ inhibitors and immunosuppressants.

T CELL IL-2 ASSAY

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3\times10^6$ ml in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 $\mu$l/well. The various dilutions of test compound were then added in triplicate wells at 25 $\mu$l/well, incubated for 30 min at 37° C. Ionomycin (125 ng/ml), and PMA (1 or 5 ng/ml), were added to the appropriate wells. The culture plates were then incubated at 37° C. in a humidified atmosphere of 5% $CO_2$–95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, Minn.). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T CELL PROLIFERATION ASSAY

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at $4-4.5\times10^6$ cells/ml in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, N.Y.). After washing 2× with complete media, these purified T cells were also resuspended at $2-2.5\times10^6$ cells/ml in complete media. The various dilutions of the compound were added in triplicates at 50 ul/well of a 96 well flat-bottom microculture plate (Costar, Cambridge, Mass.). T cell suspension was then immediately distributed into the wells at 100 $\mu$l/well. After incubating the cells with compound for 30 min. at 37° C. in a humidified atmosphere of 5% $CO_2$–95% air, 20 $\mu$l/well of anti-CD3 (Ortho Diagnostic, N.J.) at final conc. of 0.3 ng/ml was added, followed by 50 $\mu$l of the irradiated MNC. The culture plates were then incubated at 37° C. in a humidified atmosphere of 5% $CO_2$–95% air for 72 hours. The proliferation of T lymphocytes was assessed by measurement of tritiated thymidine incorporation. During the last 18–24 hrs. of culturing, the cells were pulse-labeled with 2 $\mu$Ci/well of tritiated thymidine (NEN, Cambridge, Mass.). The cultures were harvested on glass fiber filters using a multiple sample harvester (MACH-II, Wallac, Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

KV1.3-RUBIDIUM EFFLUX ASSAY

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$ (3 $\mu$Ci/ml, Dupont-NEN) in the glutamine supplemented IMDM. After aspiration of the media, 100 $\mu$l of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 $\mu$l test samples in Low K Buffer also containing 0.2% BSA and 2 mM ouabain. Samples are tested at either 1 $\mu$g/ml for routine screening or at a variety of concentrations encompassing at least ⅒ to 10 times the putative $IC_{50}$ of test compound to determine potency. After a fixed preincubation time, which is usually 10 min, the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, 10 HEPES, pH adjusted to 7.2 with NaOH) also containing test compounds. To measure $^{86}Rb^+$ efflux through the channels, aliquots of 100 μl are taken from each well after a given time and added to plates containing 100 μl MicroScint-40 (Packard) for counting by liquid scintillation techniques. MicroScint-40 (100 μl) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}$=100 pM).

DOSAGE FORMS

As an immunosuppressive, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto.

EXAMPLE 1

A Method Of Extracting The Compounds Of Formula 1(a) and 1(b) From *Spachea correa*

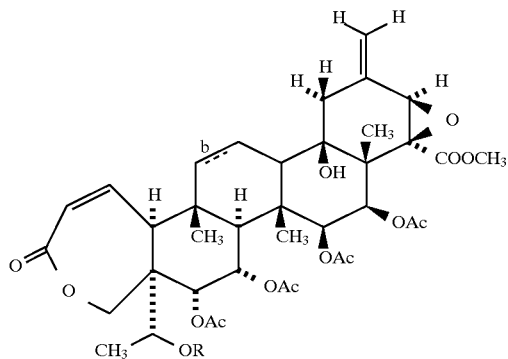

One gram of an ethanol extract of the roots of *Spachea correa* was partitioned between 100 ml of hexane (twice) and 100 ml of 90% aqueous methanol. After separation of the phases, the defatted methanol was concentrated down under vacuum to give an aqueous suspension. This was diluted out to 100 ml with water and extracted, with 100 ml of methylene chloride.

The bioactive methylene chloride extract was dried down to give 12 mg of residue. This was first fractionated by preparative thin layer chromatography (TLC) on a 20 cm by 20 cm E. Merck silica gel $60F_{254}$ plate of 1 mm thickness using methylene chloride-ethyl acetate 1:1 (v/v) as solvent, then by high performance liquid chromatography (HPLC) using a Zorbax $RxC_8$ 4.6 mm×25 cm column, operated at 50° C. and eluted with a 50 minute gradient of acetonitrile:water (1:1, v/v) to 100% acetonitrile, delivered at 1 ml/min, to afford 4 mg of compound 1(a) and 1 mg of 1(b).

Homogeneity of the preparations was ascertained in several TLC systems, such as E. Merck silica gel $60F_{254}$, methylene chloride-ethyl acetate 1:1, Rf 1(a) 0.4, Rf 1(b) 0.3; Whatman $KC_{18}$, methanol-water 9:1, Rf 1(a) 0.65, Rf 1(b) 0.75 and by HPLC using a Zorbax $RxC_8$ column, acetonitrile-water 3:2, k' 1(a) 4.15, k' 1(b) 3.30; and by NMR.

Mass spectra were recorded on JEOL SX-102A (electron impact, EI,903V) and JEOL HX110 (Fast Atom Bombardment, FAB) mass spectrometers. Exact mass measurements were performed at high resolution (HR-EI) using perfluorokerosene (PFK) as the internal standard. Trimethylsilyl derivatives were prepared with a 1:1 mixture of BSTFA-pyridine at room temperature The FAB spectrum was run in a matrix of dithiothreitol (20/80).

The compound of Formula 1(a) runs underivatized by EI. The molecular ion is observed a m/z 788 and three successive loses of acetic acid are observed. The base peak is observed a m/z 334. The compound does not silylate. Scanning HR-EI indicated a molecular formula of $C_{40}H_{52}O_{16}$. A table of the critical HR-EI data is given below.

| Observed m/z | Formula | Assignment |
| --- | --- | --- |
| 788.3220 | $C_{40}H_{52}O_{16}$ | $M^+$ |
| 728.3040 | $C_{38}H_{48}O_{14}$ | M-acetic acid |
| 668.2834 | $C_{36}H_{44}O_{12}$ | M-2 × acetic acid |
| 334.1417 | $C_{18}H_{22}O_6$ | base peak |

$^{13}C$ NMR spectra were recorded for the compound of Formula 1(a) in $CD_2Cl_2$ at 100 MHz on a Varian Unity 400 NMR spectrometer at 20° C. Chemical shifts are given in ppm relative to tetramethylsilane (TMS) at zero ppm using the solvent peak at 53.8 ppm as internal standard. The following data were observed: 15.0, 15.2, 16.8, 17.1, 20.7*, 20.9, 21.1, 21.6, 21.8, 22.2, 35.6, 40.8*, 42.1, 43.6, 45.1, 47.5, 49.3*, 53.5, 59.1, 62.6, 63.5, 66.1, 66.7*, 68.4*, 69.9, 73.9, 75.0, 75.6,77.1*, 119.4, 123.7, 138.9, 143.0, 167.7, 169.2, 169.3*, 170.25, 170.31, 170.8, 171.3 ppm (where the * signifies the observation as broad resonances). The carbon count of 40 is in agreement with the molecular formula $C_{40}H_{52}O_{16}$ derived by scanning HR EI-MS.

The $^1H$ NMR spectra of compound of Formula(a) is provided as FIG. 1. The spectra was recorded at 400 MHz in $CD_2Cl_2$ on a Varian Unity 400 NMR spectrometer at 25° C. Chemical shifts are in ppm relative to TMS at zero ppm using the solvent peak at δ5.32 as the internal standard.

The mass spectra of compound of Formula 1(b) was obtained as above. The following results were obtained.

| Observed m/z | Formula | Assignment |
|---|---|---|
| 786.3075 | $C_{40}H_{50}O_{16}$ | $M^+$ |
| 726.2886 | $C_{38}H_{46}O_{14}$ | M-acetic acid |
| 666.2651 | $C_{36}H_{42}O_{12}$ | M-2 × acetic acid |
| 606.2451 | $C_{34}H_{38}O_{10}$ | M-3 × acetic acid |
| 489.2099 | $C_{26}H_{33}O_9$ | base peak |
| 471.1992 | $C_{26}H_{31}O_8$ | |

$^{13}C$ NMR spectra were recorded for the compound of Formula 1(b) using the procedure described above. The following results were observed: 14.8, 14.9, 17.3, 20.8, 20.9, 21.3, 21.7, 21.8, 21.9, 27.1, 35.1, 40.6, 42.3, 45.4, 48.1, 50.4, 53.5, 54.1, 57.8, 63.7, 66.2, 67.8, 68.6, 71.4, 73.3, 73.8, 74.4, 119.5, 121.1, 124.3, 137.1, 138.9, 143.3, 167.6, 168.6, 169.3, 169.5, 169.9, 171.0, 171.7 ppm.

The carbon count of 40 is in agreement with the molecular formula $C_{40}H_{50}O_{16}$ derived by scanning HR EI-MS.

EXAMPLE 2
A Method Of Extracting The Compounds Of Formula 1(c) And 1(d) From *Spachea Correa*

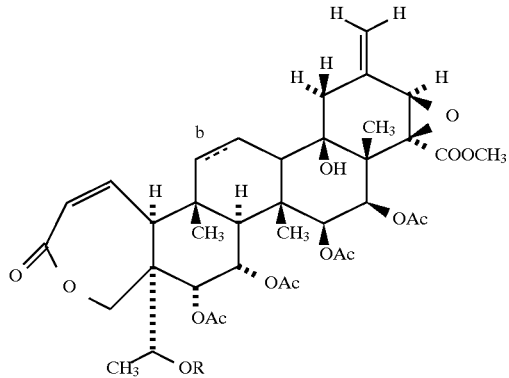

Analogs of the compounds of Formula 1(a) and 1(b) could be detected in the crude extract and fractions thereof when the process of Example 1 was carried out on a larger scale. Thus, 50 g of ethanol extract were partitioned as described in Example 1 using 900 ml of each solvent at each step.

Partial purification of the methylene chloride extract was achieved by column chromatography on E. Merck silica gel 60 (120 ml), eluting with a step gradient of ethyl acetate in methylene chloride. The step gradient was designed so that the column was washed first with 100% methylene chloride and then with methylene chloride- ethyl acetate mixtures of 9:1, 8:2, 3:2, 2:1, 1:1, 1:2, 2:8 and 1:9. Ultimately the column was washed with 100% ethyl acetate. Fractions eluted with methylene chloride-ethyl acetate 3:2 were enriched in compound of Formula 1(a) and 1(b). These were resolved by HPLC using a Zorbax $RxC_8$ 9 mm×25 cm column, maintained at 50° C. and eluted at 4 ml/min with acetonitrile-water 1:1 v/v. Three identical runs finally afforded 100 mg and 20 mg respectively of 1(a) and 1(b) after crystallization from methanol. Later-eluting fractions from the silica gel column above were found to contain at least two related compounds based on UV spectra and color reactions on TLC plates. Material from the methylene chloride-ethyl actate 1:1 and 1:2 washings were combined and evaporated down. Separation was achieved on the same HPLC column as above, eluting with a 50 minute gradient of 30% to 50% acetonitrile in water. Two identical runs gave 6 mg of purified compound 1(c). Fractions containing the compound of Formula 1(d) were again processed by HPLC (same column) using acetonitrile-water 3:7 delivered isocratically, to yield 2 mg of purified Formula 1(d).

The mass spectra of these compounds were recorded on a Finnigan TSQ700 mass spectrometer (electrospray ionization, ESI). The samples were analyzed by LC/MS using a 2.1×150 mm $C_8$ column at 0.2ml/min. with a mobile phase of 45% acetonitrile/0.01M aqueous ammonium acetate at 50° C. Component 1(d) had a retention time of 10.5 min. and a molecular weight of 744 which is observed a m/z: 745 ($M^+H$), 762 ($M^+NH_3$), 786 ($M^+H^+MeCN$). Component 1(c) has a retention time of 11.8 and a molecular weight of 746 which is observed at m/z: 747 ($M^+H$), 764 ($M^+NH_3$) and 788 ($M^+H^+MeCN$).

The $^{13}C$ NMR spectra obtained for the compound of Formula 1(c) using the conditions previously described is as follows: 15.1 (2×), 16.9, 19.8, 20.8, 20.91, 20.94, 21.9, 22.3, 35.6, 40.6, 42.2, 43.9, 45.0, 47.7, 50.8, 53.5, 55.6, 61.8, 63.5, 66.0, 67.6 (2×), 69.8, 70.0, 73.9, 75.0, 75.6, 119.3, 123.7, 139.0, 144.4, 167.8, 169.2, 169.5, 170.1, 170.4, 171.4 ppm.

The carbon count of 38 is in agreement with the molecular formula $C_{38}H_{50}O_{16}$ derived by scanning HR EI-MS.

EXAMPLE 3
Separation BY HPLC

Compounds of this invention were characterized by the following behavior during HPLC separation on a Zorbax $RxC_8$ 4.6 mm×25 cm column, maintained at 50° C. and eluted at 1 ml/min with acetonitrile-water 3:2 v/v): Compound 1(a): k'=4.15; 1(b): k'=3.30; 1(c): k'=2.30; 1(d): k'=2.10.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE 4
Additional Purification Procedure

A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloride-methanol 97:3 in a first step; the mixed compounds of Formula 1(a) and 1(b) thus obtained are resolved by chromatographing on fresh silica gel eluted with methylene chloride-ethyl acetate 3:1. Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

EXAMPLE 5

6,7,15,16-Tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-dien-3-one

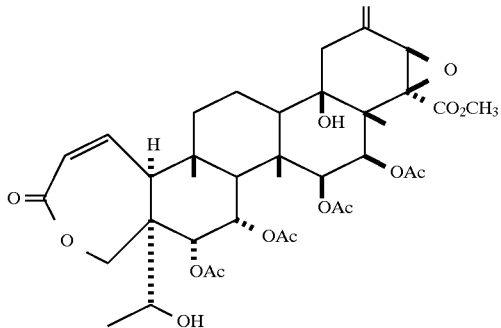

A solution of 102.1 mg (0.130 mmole) of 4,6,7,15,16-pentakis (acetyloxy)-21,22-epoxy-18-hydroxy-22-methoxycarbonyl-[6α,7α,15β,16β,21β,22β]D:A-Friedo-A-homo-27,30-dinor-24-oxaoleana-1,20(29)-dien-3-one in 4 mL of tetrahydrofuran and 2 mL of 3M aqueous HCl was heated at 40° C. for 24 h. The solution was diluted with dichloromethane and the layers were separated. The organic layer was washed with O.1M phosphate buffer (pH 7), then was dried over $MgSO_4$ and concentrated. The residue was purified by silica gel chromatography with 2:1 ethyl acetate-hexane to afford 44.9 mg of the title compound as a white solid (46%); $^1H$ NMR ($CDCl_3$) δ4.20 (q, 1H, J=4.3 Hz, C4-H); Mass Spectrum (APCI): m/e 764 ($M^+NH_4$).

EXAMPLE 6

4-Benzoyloxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

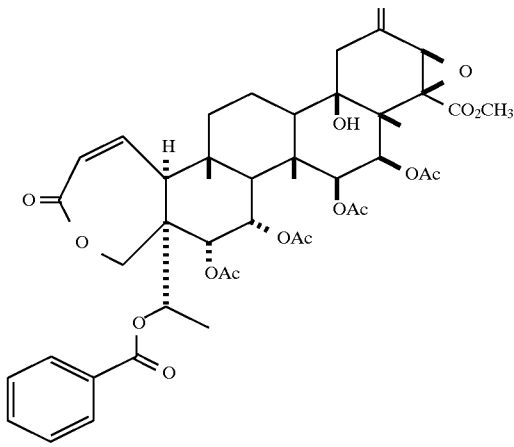

To a solution of 17.5 mg (23.5 μmole) of 6,7,15,16-tetrakis (acetyloxy)-21,22-epoxy-4,18-dihydroxy-22-methoxycarbonyl-[6α,7α,15β,16β,21β,22β]D:A-Friedo-A-homo-27,30-dinor-24-oxaoleana-1,20(29)-dien-3-one in 0.5 mL pyridine was added 27.5 mL (237 μmole) of benzoyl chloride. The solution was stirred at room temperature for 4 h, then was concentrated under reduced pressure. The residue was first filtered through a plug of silica gel and then purified by HPLC (Waters RCM, μ Porosil, 10 mm×10 cm) using a mixture of 9.6:6 (5:4:1 hexane-methyl tert-butyl ether-acetonitrile:hexane) to afford 17.3 mg (88%) of the title compound as a white solid; $^1H$ NMR ($CDCl_3$) δ5.67 (1H, C4-H), 7.50 (t, 2H, J=7.6 Hz), 7.63 (t, 1H, J=7.5 Hz), 8.09 (d, 2H, J=7.3 Hz); $^1H$ NMR ($CD_2Cl_2$) δ5.65 (q, 1H, J=6.0 Hz, C4-H), 7.51 (t, 2H, J=7.5 Hz), 7.64 (m, 1H), 8.03 (dd, 2H, J=1, 7.5 Hz); Mass Spectrum (CI, $NH_4OAc$): m/e 868 ($M^+NH_4$).

Examples 7 through 30 were prepared using the procedures described in Example 6 with the appropriate acid chloride.

EXAMPLE 7

4-(2-Chlorobenzoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

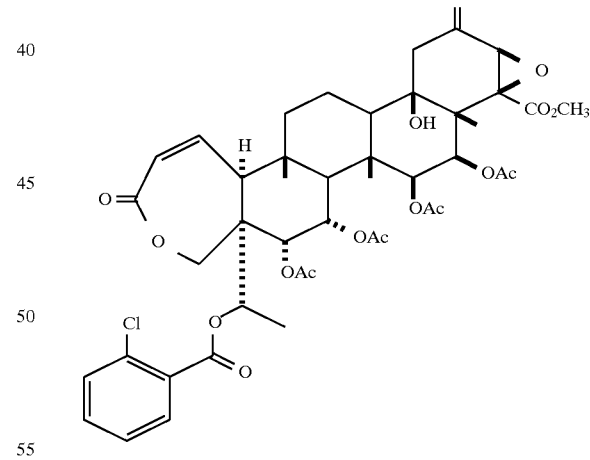

$^1H$ NMR δ7.37 (t, 1H, J=7 Hz), 7.48–7.53 (m, 2H), 7.83 (d, 1H, J=8 Hz); Mass Spectrum (APCI): m/e 902 ($M^+NH_4$).

EXAMPLE 8

4-(4-Methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

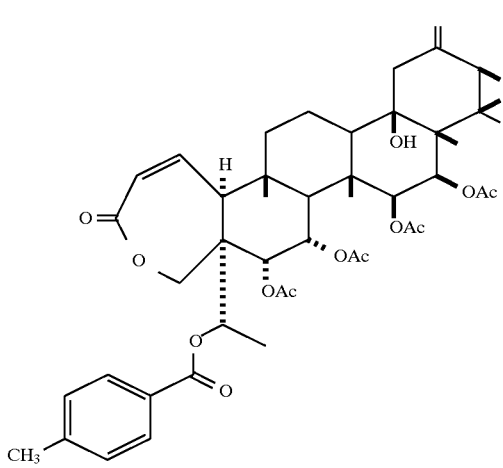

$^1$H NMR δ7.30 (d, 2H, J=8 Hz), 7.9 (d, 2H, J=8 Hz); Mass Spectrum (APCI): m/e 882 (M$^+$NH$_4$).

EXAMPLE 9

4-(2-methoxyacetyloxy)-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

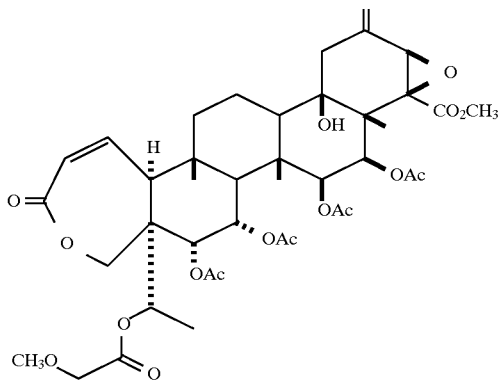

$^1$H NMR δ5.62 3.49 (s, 3H, CH$_2$OC$\underline{H}_3$)(1H, H4); Mass Spectrurm (APCI): m/e 836 (M$^+$NH$_4$).

EXAMPLE 10

4-(2-Chloroacetyloxy-6,7,15,16-tetrakis(acetyloxy)-21,22-epoxy-18-hydroxy-22-methoxycarbonyl[6α,7α,15β,16β,21β,22β]D:A-Friedo-A- homo-27,30-dinor-24-oxaoleana-1,20(29)-dien-3-one

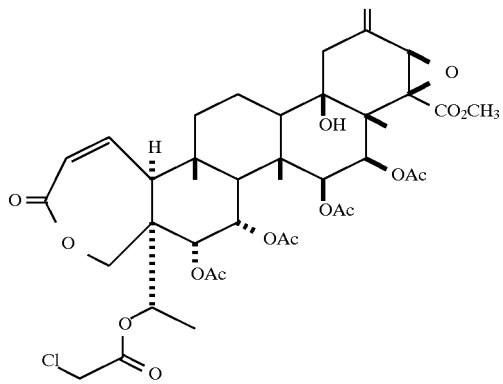

$^1$H NMR δ5.65 4.09–4.15 (m, 2H, —C$\underline{H}_2$Cl)(1H, H4); Mass Spectrwm (APCI): m/e 840, 842 ($^{35}$Cl—M$^+$NH$_4$, $^{37}$Cl—M$^+$NH$_4$).

EXAMPLE 11

4-(4-Bromobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

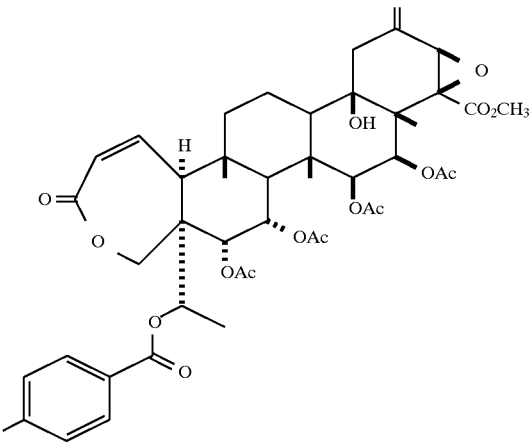

$^1$H NMR δ7.66 (d, 2H, J=8.5Hz), 7.88 (d, 2H, J=8.5 Hz).

EXAMPLE 12

4-(4-Cyanobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

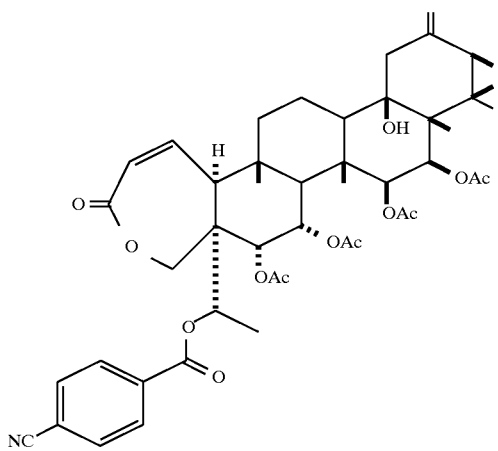

$^1$H NMR δ5.68 (1H, C4-H), 7.81 (d, 2H, J=8 Hz), 8.12 (d, 2H, J=8 Hz); Mass Spectrum (APCI): m/e 893 (M$^+$NH$_4$).

EXAMPLE 13

4-(Propanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

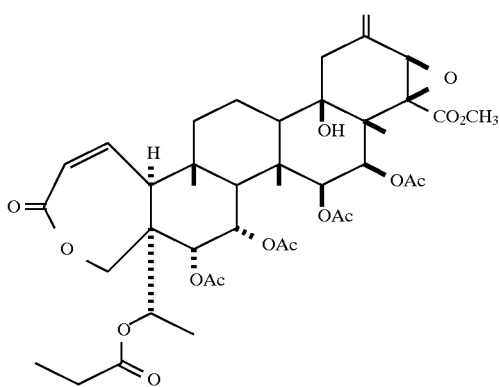

$^1$H NMR δ1.19 (t, 3H, J=6 Hz, —CH$_2$CH$_3$), 2.36–2.41 (m. 3H, —CH$_2$CH$_3$ and H-10); Mass Spectrum (APCI): m/e 820 (M$^+$NH$_4$).

EXAMPLE 14

4-(2,2-Dimethylpropanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

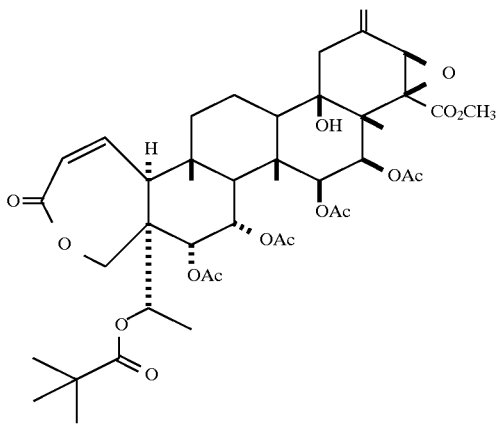

$^1$H NMR δ1.24 (s, 9H, —C(CH$_3$)$_3$), 5.46 (q, 1H, J=7 Hz, C4-H); Mass Spectrum (APCI): m/e 848 (M$^+$NH$_4$).

EXAMPLE 15

4-Cyclohexylcarbonyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

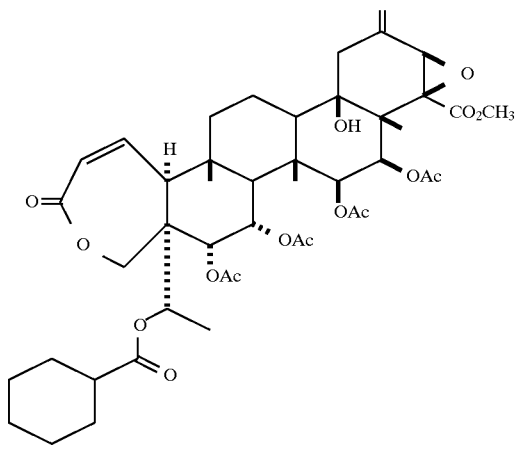

$^1$H NMR δ5.44 (q, 1H, J=4.8 Hz, C4-H); Mass Spectrum (APCI): m/e 874 (M$^+$NH$_4$).

EXAMPLE 16

4-(2-Methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

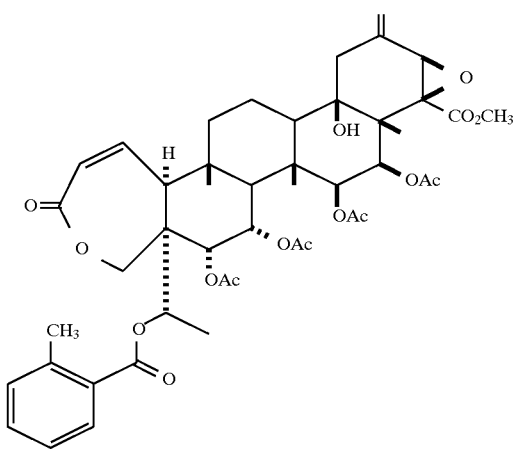

$^1$H NMR δ2.68 (s, 3H), 5.73 (q, 1H, J=6.4 Hz, C4-H), 7.28 (dd, 1H, J =7.5, 7.5 Hz), 7.32 (d, 1H, J=7.8 Hz), 7.47 (dd, 1H, J=7.5, 7.0 Hz), 7.87 (d, 1H, J=8.0 Hz); Mass Spectrum (APCI): m/e 882 (M$^+$NH$_4$).

EXAMPLE 17

4-(2-Methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

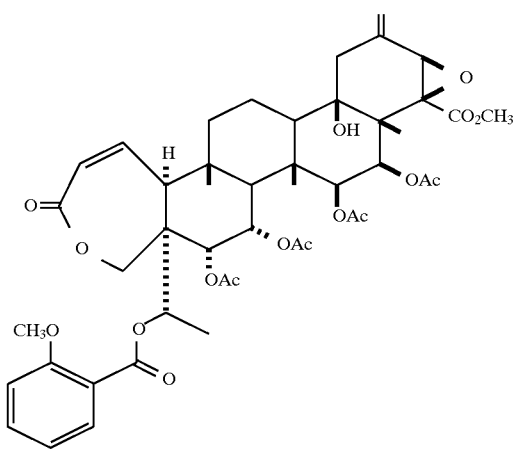

$^1$H NMR δ3.93 (s, 3H), 7.02 (dd, 1H, J=7.0, 6.5 Hz), 7.05 (d, 1H, J=8.5 Hz) 7.56 (dd, 1H, J=7.5, 6.5 Hz) 7.85 (dd, 1H, J=7.7, 1.3 Hz); Mass Spectrum (APCI): m/e 898 (M$^+$NH$_4$).

EXAMPLE 18

4-(2-Nitrobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

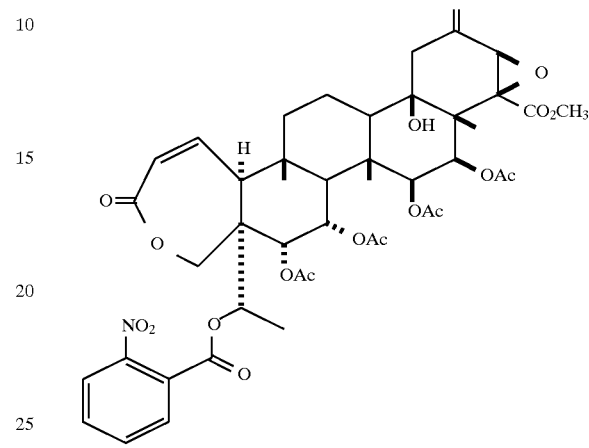

$^1$H NMR δ5.65 (1H, C4-H), 7.67–7.75 (m, 3H), 7.98 (d, 1H, J=8.3 Hz); Mass Spectrum (APCI): m/e 913 (M$^+$NH$_4$).

EXAMPLE 19

4-(3-Methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

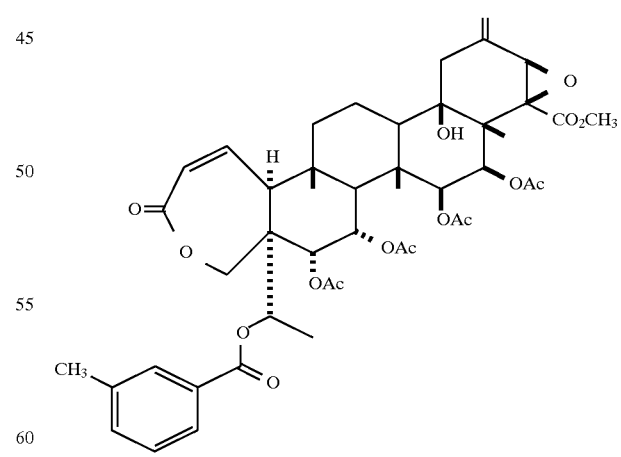

$^1$H NMR δ2.44 (s, 3H), 7.38 (dd, 1H, J=7.5, 7.6 Hz), 7.44 (d, 1H, J=7.5 Hz), 7.81 (d, 1H, J=7.6 Hz), 7.83 (s, 1H); Mass Spectrum (APCI): m/e 882 (M$^+$NH$_4$).

EXAMPLE 20

4-(4-Methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

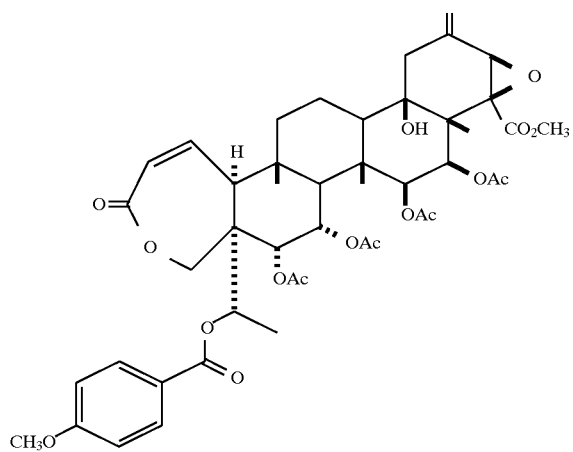

$^1$H NMR δ3.90 (s, 3H), 5.68 (1H, C4-H), 6.97 (d, 2H, J=9 Hz), 7.96 (d, 2H, J=9 Hz); Mass Spectrum (APCI): m/e 898 (M$^+$NH$_4$).

EXAMPLE 21

4-(2-Bromobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

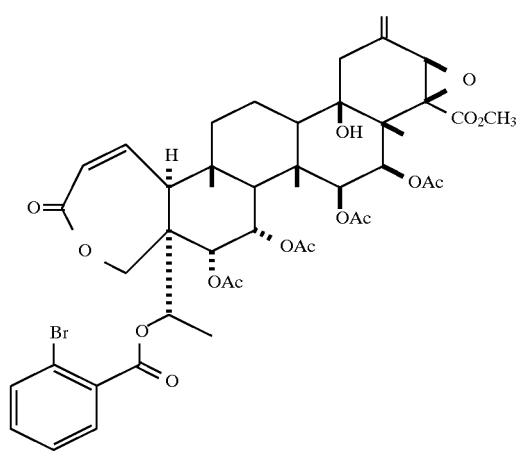

$^1$H NMR δ5.67 (1H, C4-H), 7.40–7.43 (m, 2H), 7.72 (dd, 1H, J=2.2, 6.9 Hz), 7.78 (dd, 1H, J=2.3, 6.9 Hz); Mass Spectrum (APCI): m/e 946, 948 ($^{79}$Br-M$^+$NH$_4$, $^{81}$Br-M$^+$NH$_4$).

EXAMPLE 22

4-(2,3-Difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

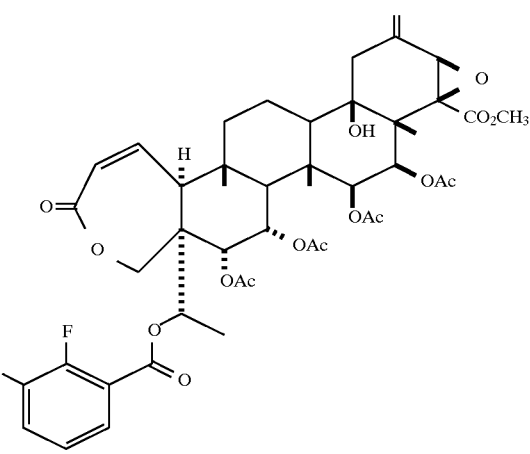

$^1$H NMR δ7.73(dd, 1H, J=7.5, 6.5 Hz), 7.41–7.46 (m, 1H), 7.20–7.24 (m, 1H); Mass Spectrum (APCI): 904 (M$^+$NH$_4$).

EXAMPLE 23

4-(3-Methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

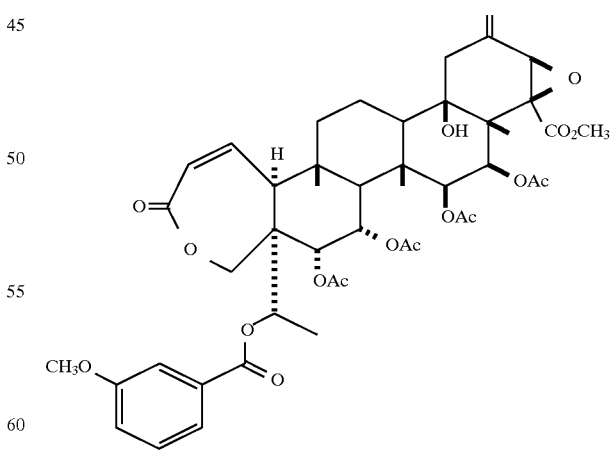

$^1$H NMR δ3.87 (s, 3H), 7.16 (dd, 1H, J=2.6, 8.3 Hz), 7.40 (dd, 1H, J =7.8, 8.3 Hz), 7.53 (s, 1H), 7.59 (d, 1H, J=7.8 Hz); Mass Spectrum (APCI): m/e 898 (M$^+$NH$_4$).

EXAMPLE 24

4-(1-Naphthoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

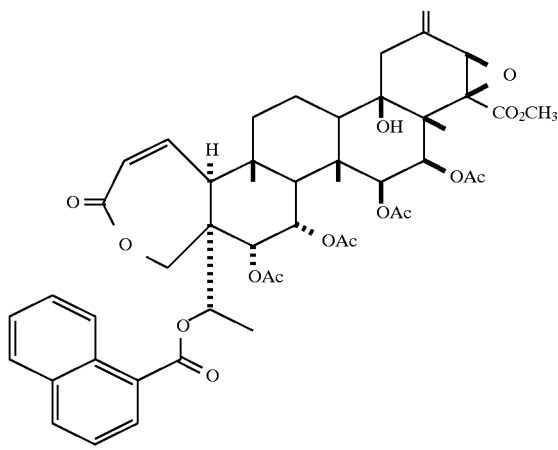

$^1$H NMR δ5.87 (q, 1H, J=5.9 Hz, C4-H), 7.54 (t, 1H, J=7.8 Hz), 7.61 (t, 1H, J=8.0 Hz), 7.70 (dt, 1H, J=1.1, 8.2 Hz), 7.95 (d, 1H, J=8.2 Hz), 8.10 (d, 1H, J=8.2 Hz), 8.18 (dd, 1H, J=1.1, 7.3 Hz), 9.14 (d, 1H, J=8.7 Hz); Mass Spectrum (APCI): m/e 918 ($M^+NH_4$).

EXAMPLE 25

4-(2-Naphthoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

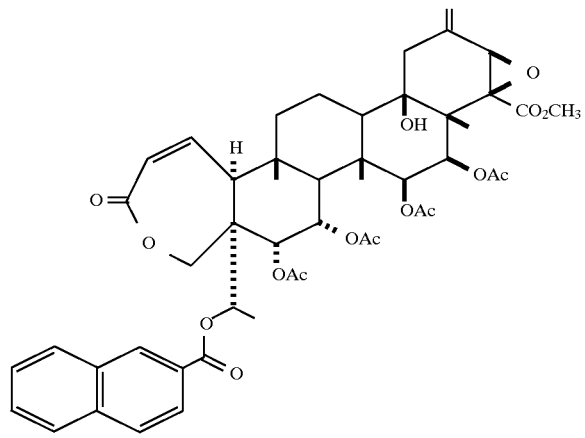

$^1$H NMR δ5.72 (1H, C4-H), 7.61 (t, 1H, J=7.5 Hz), 7.65 (t, 1H, J=7.1 Hz), 7.92 (d, 1H, J=8.7 Hz), 7.94 (d, 1H, J=8.9 Hz), 7.97 (d, 1H, J=8.2 Hz), 8.02 (d, 1H, J=8.4 Hz), 8.58 (s, 1H); Mass Spectrum (APCI): m/e 918 ($M^+NH_4$).

EXAMPLE 26

4-(2-Iodobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

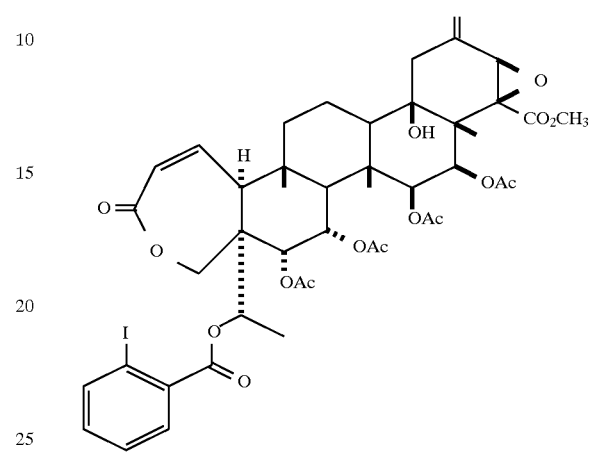

$^1$H NMR δ5.66 (1H, C4-H), 7.21 (td, 1H, J=1,6, 7.2 Hz), 7.44 (t, 1H, J=7.8 Hz), 7.76 (t, 1H, J=7.8 Hz), 8.06 (d, 1H, J=7.8 Hz); Mass Spectrum (APCI): m/e 994 ($M^+NH_4$).

EXAMPLE 27

4-(2-Trifluoromethylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

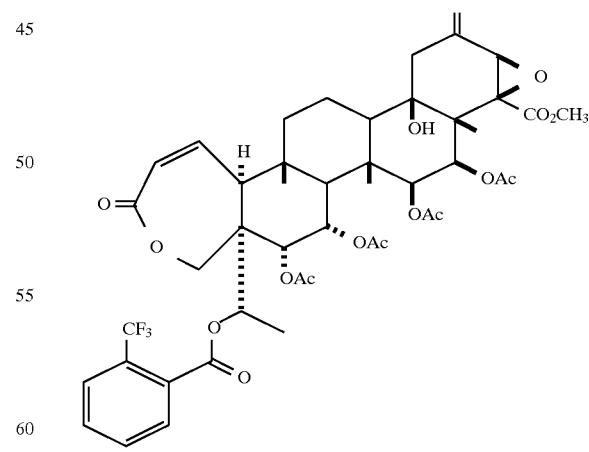

$^1$H NMR δ7.81 (dd, 1H, J=4.5, 4.5 Hz), 7.73 (dd, 1H, J=5.5, 4.0 Hz), 7.65–7.68 (m, 2H), 5.83 (1H, C4-H); Mass Spectrum (APCI): 936 ($M^+NH_4$).

EXAMPLE 28

4-(Pentanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

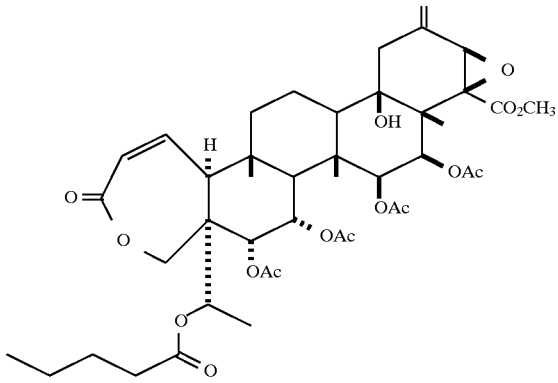

$^1$H NMR δ0.95 (t, 3H, J=7.4 Hz), 2.33(t, 2H, J=7.3 Hz), 5.46 (1H, C4-H); Mass Spectrum (APCI): m/e 848 (M$^+$NH$_4$).

EXAMPLE 29

4-(2-Fluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

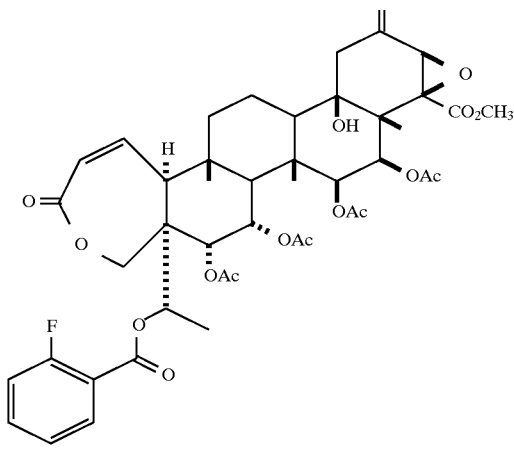

$^1$H NMR δ4.28, 4.71 (dd, AB, 2H, J=12 Hz, C24-CH$_2$), 5.22 (s, 1H, C29-H), 5.53 (s, 1H, C29-H), 5.66 (1H, C4-H), 6.09 (d, 1H, J=12.0 Hz, C2-H), 6.28 (dd, 1H, J=8.5, 12.0 Hz, C1-H), 7.20 (m, 1H), 7.29 (m, 1H), 7.61 (m, 1H), 7.97 (M, 1H); Mass Spectrum (APCI): m/e 886 (M$^+$NH$_4$).

EXAMPLE 30

4-(2-Furoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

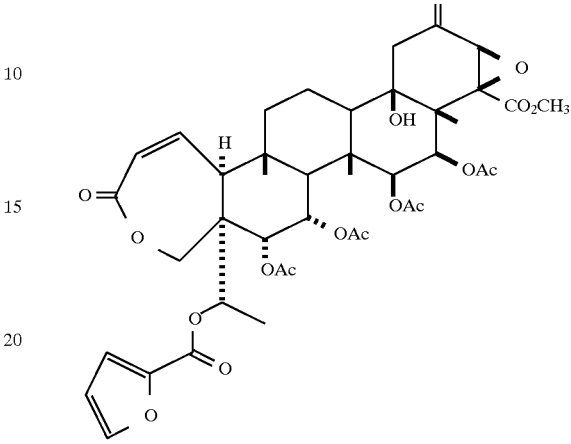

$^1$H NMR δ5.68 (1H, C4-H), 6.57 (dd, 1H, J=1, 3.5 Hz) 7.15 (d, 1H, J=3.5 Hz), 7.66 (d, 1H, J=1 Hz); Mass Spectrum (APCI): m/e 858 (M$^+$NH$_4$).

EXAMPLE 31

4-(Benzyloxycarbonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

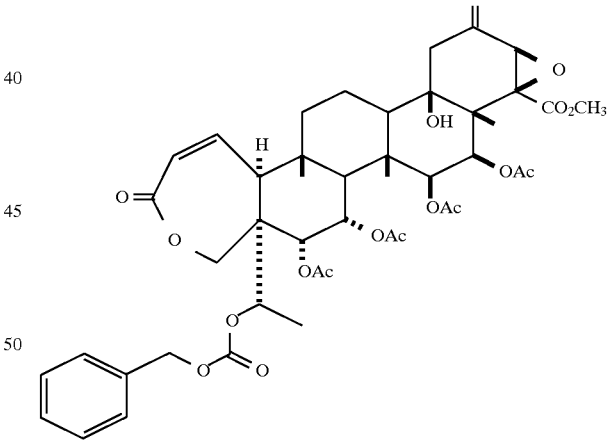

A solution of 15 mg (20 μmole) of 6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-dien-3-one and 3.2 mg (60 μmole) of 1, 1'-carbonyl diimidazole in 2 mL benzene was heated at 60° C. for 4 h. Then 200 μL of benzyl alcohol and 23 μL triethyl amine were added and the solution was stirred at 60° C. After 18 h, the mixture was filtered through silica gel using 30% acetone-hexane and the solvent was concentrated. The residue was purified by HPLC (Waters RCM, μ Porosil, 10 mm×10 cm) using a mixture of 2:1 (5:4:1 hexane-methyl tert-butyl ether-acetonitrile:hexane) to afford 13 mg (75%) of the title compound as a white solid; ¹H NMR (CDCl₃) δH NMR (CDCl₃) δ5.22 (s, 2H); δ5.31 (q, 1H, J=6.5 Hz, C4-H); δ7.41–7.44 (m, 5H) Mass Spectrum (APCI): m/e 898 (M⁺NH₄).

EXAMPLE 32

4-(Benzyloxymethyl)oxy-6,7,15,16-tetrakis(acetyloxy)-21,22-epoxy-18-hydroxy-22-methoxycarbonyl[6α,7α,15β,16β,21β,22β]D :A-Friedo-A-homo-27,30-dinor-24-oxaoleana-1,20(29)-dien-3-one

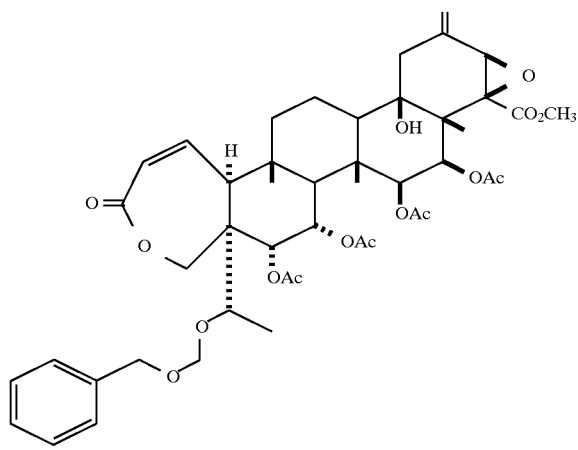

A solution of 20 mg (27 [mole) of 6,7,15,16-tetrakis(acetyloxy)-21,22-epoxy-4,18-dihydroxy-22-methoxycarbonyl]6α,7α,15β,16β,21β,22β]D:A-Friedo-A-homo-27,30-dinor-24-oxaoleana-1,20(29)-dien-3-one and 12 μL (95 μmole) of N,N dimethylaniline in 1 mL dichloromethane was treated with 12 μL (87 μmole) benzylchloromethyl ether and the solution stirred overnight at room temperature. The solution was then treated with another 12 μL each of N,N dimethylaniline and benzylchloromethyl ether and allowed to stir 6 hours at room temperature. The reaction was partitioned between 20 ml ethyl ether and 10 ml water and separated. The aqueous layer was washed with 5 ml ether and the organic layers were combined. The combined organic layer was washed with 5 ml 2N H₂SO₄, brine and dried over MgSO4 and concentrated. The residue was purified by HPLC (Waters RCM, μ Porosil, 10 mm×10 cm) using a mixture of 2:1 (5:4:1 hexane-methyl tert-butyl ether-acetonitrile:hexane) to afford 13 mg (75%) of the title compound as a white solid; ¹H NMR (CDCl₃).

δ4.21 (q, 1H, J=6 Hz), δ4.67 ,4.70 (dd ,AB 2H, J=12 Hz), δ4.84, 4.88 (dd, AB, 2H, J=7 Hz), δ7.28–7.42 (m,5H); Mass Spectrum (APCI): m/e 884 (M⁺NH₄).

EXAMPLE 33

4-Methanesulfonyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

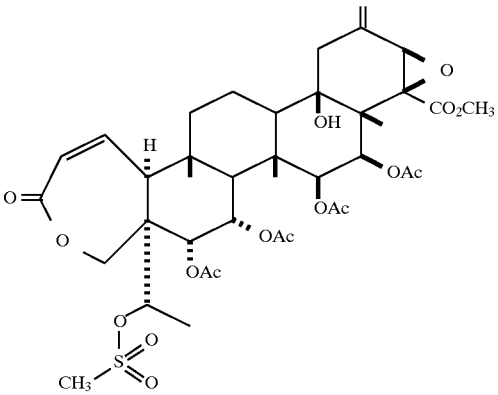

A solution of 4-methanesulfonyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one (11.1 mg) in 1.0 ML of CH₂CL₂ was added Et₃N (62.2 uL) and MsCl (23 uL). The solution was stirred at room temperature for 16 h, then was concentrated under reduced pressure. The residue was purified by flash chromatography with 33% hexane in ethyl acetate to afford 12.4 mg (100%) of the title compound as a oil; Mass Spectrum (APCI): m/e 842 (M⁺NH₄).

Examples 34 through 40 were prepared using the procedure described in Example 33.

EXAMPLE 34

4-(4-Methylbenzenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

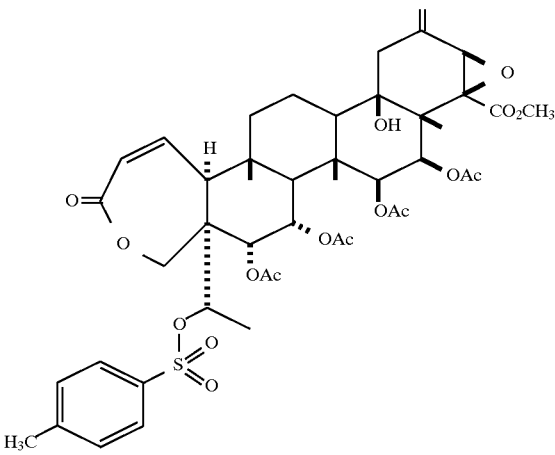

¹H NMR (CDCl₃) δ2.46 (s, 3H), 5.31 (q, 1H, J=6 Hz), 7.38 (d, 2H, J=8 Hz), 7.84 (d, 2H, J=8 Hz) Mass Spectrum (APCI): m/e 918 (M⁺NH₄).

EXAMPLE 35

4-(Phenylmethanesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

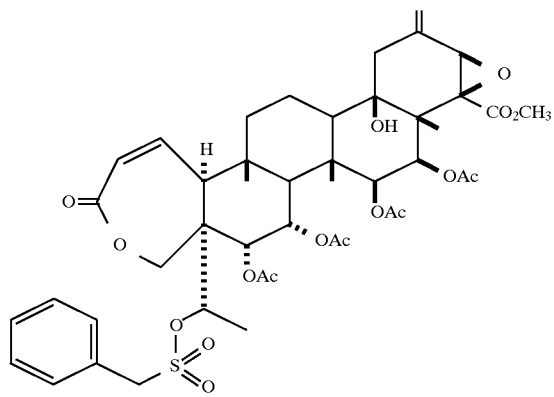

$^1$H NMR (CDCl$_3$) δ4.37 (s, 2H), 5.35 (1H, C4-H), 7.41 (s, 5H) Mass Spectrum (APCI): m/e 918 (M$^+$NH$_4$).

EXAMPLE 36

4-(4-Chlorobenzenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

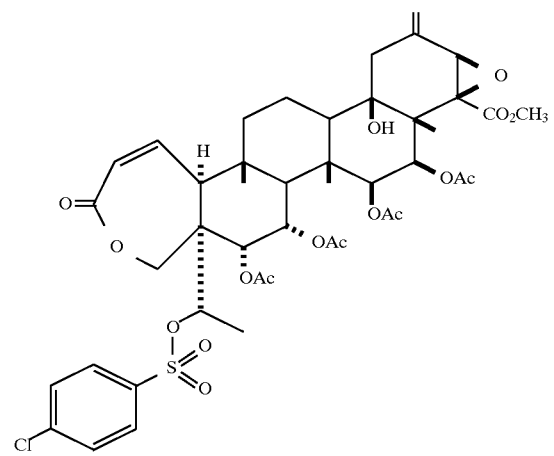

$^1$H NMR (CDCl$_3$) δ5.37 (1H, C4-H), 7.59 (d, 2H, J=8.5 Hz), 7.93 (d, 2H, J=8.5 Hz); Mass Spectrum (APCI): m/e 938 (M$^+$NH$_4$).

EXAMPLE 37

4-(4-Methoxybenzenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

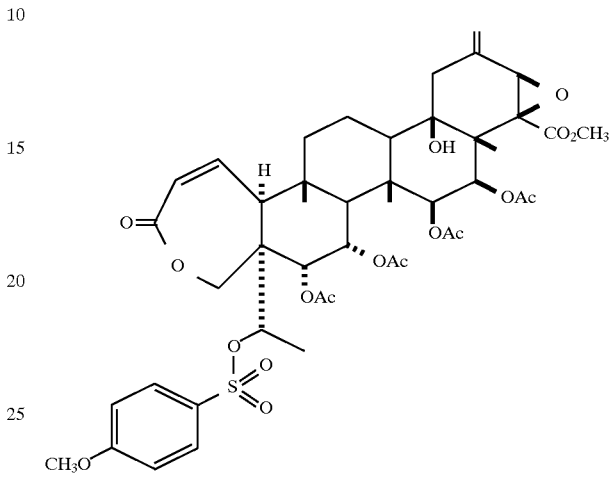

$^1$H NMR (CDCl$_3$) δ (s, 3H), 5.62(1H, C4-H), 7.09 (d, 2H, J=9 Hz), 7.94 (d, 2H, J=9 Hz); Mass Spectrum (APCI): m/e 934 (M$^+$NH$_4$).

EXAMPLE 38

4-Butanesulfonyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

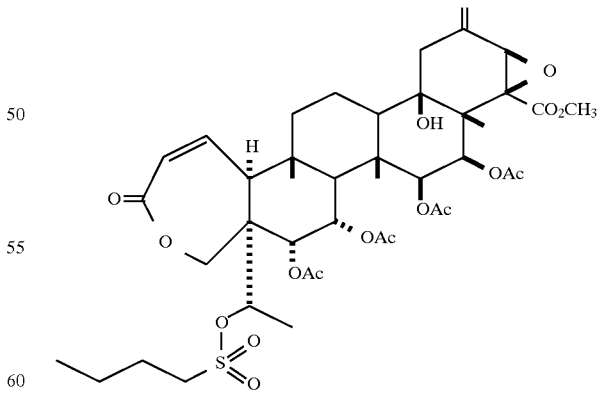

$^1$H NMR (CDCl$_3$) δ0.99 (t, 3H, J=7.5 Hz), 3.12 (t, 2H, J=7.5 Hz), 5.43 (1H, C4-H); Mass Spectrum (APCI): m/e 884 (M$^+$NH$_4$).

EXAMPLE 39

4-(2-Nitrobenzenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

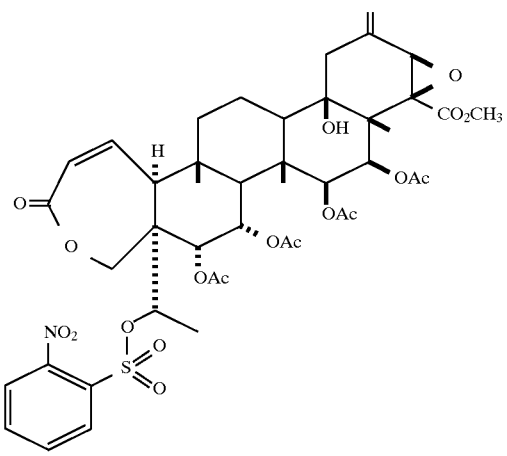

$^1$H NMR (CDCl$_3$) δ5.59 (q, 1H, J=6.5 Hz, C4-H), 7.81–7.89 (m, 3H), 8.22 (dd, 1H, J=1.5, 7.5 Hz); Mass Spectrum (APCI): m/e 949 (M$^+$NH$_4$).

EXAMPLE 40

4-(2-Thiophenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

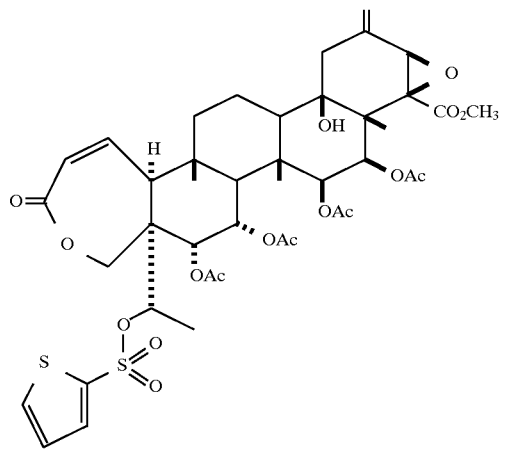

$^1$H NMR (CDCl$_3$) δ5.29 (q, 1H, J=6.0 Hz, C4-H), 7.34 (dd, 1H, J=3.5, 5 Hz), 7.86 (d, 1H, J=3.5 Hz), 7.88 (d, 1H, J=5 Hz) Mass Spectrum (APCI): m/e 910 (M$^+$NH$_4$).

EXAMPLE 41

4-(1-Imidazolylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

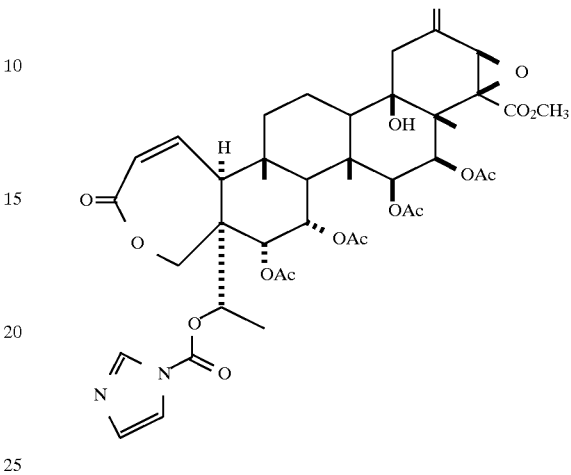

A solution of 25.2 mg (34 μmole) of 6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-dien-3-one and 27.4 mg (0.169 mmole) of carbonyl diimidazole in 2 mL of benzene was heated at 70° C. After 24 h, the solution was filtered through a pad of silica gel using 2:1 ethyl acetate-hexane and the filtrate was concentrated. The residue was purified by HPLC (Waters RCM, μ Porosil, 10 mm×10 cm) using a mixture 5:4:1 hexane-methyl tert-butyl ether-acetonitrile to afford 25.2 mg (89%) of the title compound as a white solid; $^1$H NMR (CDCl$_3$) δ5.66 (1H, C4-H), 7.12 (s, 1H), 78.39 (s, 1H), 8.11 (s, 1H) Mass Spectrum (APCI): m/e 841 (M$^+$H).

EXAMPLE 42

4-(N-Phenylmethylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

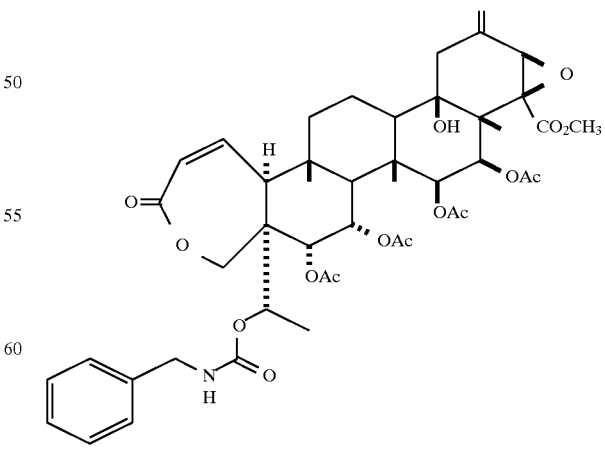

A solution of 10.8 mg (0.013) of 4-(1-imidazolyl-carbamoyl)oxy-6,7,15,16-tetrakis(acetyloxy)-21,22-epoxy- 18-hydroxy-22-methoxycarbonyl[6α,7α,15β,16β,21β,22β] D:A-Friedo-A-homo-27,30-dinor-24-oxaoleana-1,20(29)-dien-3-one in 1.0 ml of THF was added 13 μl of benzylamine and the solution was stirred at room temperature for 6 hours and at 55° C. for 14 hours. Upon removal of solvent, residue was purified by HPLC to give 3.0 mg (26%) of the title compound.

$^1$H NMR (CDCl$_3$) δ7.31–7.39 (m, 5H), 5.36 (1H, C4-H), 4.49 (dd, 1H, J=15, 6.5 Hz), 4.35–4.39 (m, 2H); Mass Spectrum (APCI): m/e 897 (M$^+$NH$_4$).

EXAMPLE 43

4-(N-Butylcarbamoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

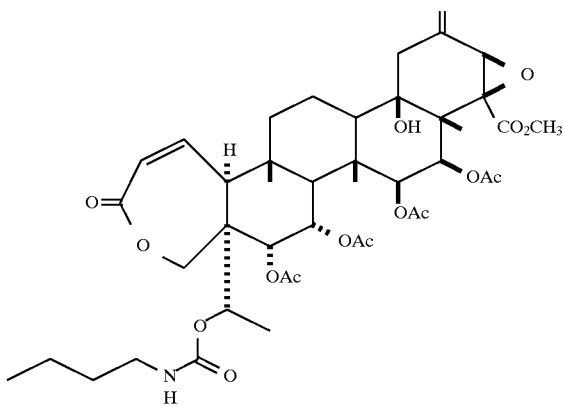

The title compound was prepared according to the procedure described in Example 42.

$^1$H NMR (CDCl$_3$) δ5.61 (1H, C4-H), 3.14–3.28 (m, 2H), 0.94 (t, 3H, J =7.1 Hz); Mass Spectrum (APCI): m/e 863 (M$^+$NH$_4$).

EXAMPLE 44

4,6,7,15,16-Pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

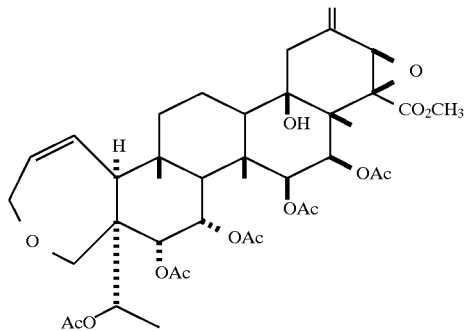

Step A 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-ol A solution of 3.0 g (3.8 mmole) of 4,6,7,15,16-pentakis (acetyloxy)-21,22-epoxy-18-hydroxy-22-methoxycarbonyl [6α,7α,15β,16β,21β,22β]D:A-Friedo-A-homo-27,30-dinor-24-oxaoleana-1,20(29)-dien-3-one in 20 mL of dry dichloromethane was cooled to 0° C. under nitrogen. Then 9 mL of a 1M solution of lithium tri-(tert-butoxy)aluminum hydride was added dropwise and the solution was stirred at 0° C. After 18 h, the reaction was quenched by dropwise addition of 20 mL of 2M aqueous H$_2$SO$_4$ and the mixture was diluted with 200 mL of ether. The layers were separated and the aqueous layer was washed with two 100 mL portions of ether. The organic layers were sequentially washed with 20 mL of 2M aqueous H$_2$SO$_4$ and brine, then were combined, dried over MgSO$_4$, and concentrated to afford 2.9 g (99%) of the title compound, which was used directly in the next step.

Step B 4,6,7,15,16-Pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene A sample of 2.9 g of crude 4,6,7,15,16-pentakis (acetyloxy)-21,22-epoxy-18-hydroxy-22-methoxycarbonyl [6α,7α,15β,16β,21β,22β]D:A-Friedo-A-homo-27,30-dinor-24-oxaoleana-1,20(29)-dien-3-ol was dissolved in 10 mL of dry dichloromethane under nitrogen. To this was added 10 mL of triethylsilane, and the solution was stirred at room temperature for 10 min. Then 2 mL (20 mmole) of boron trifluoride etherate was added and the mixture was stirred at room temperature for 15 min. The reaction was quenched by addition of 10 mL of saturated aqueous KHCO$_3$ solution and the resulting mixture was partitioned between ether and water. The water layer was washed with ether and the organic extracts were washed with brine, then were combined, dried over MgSO$_4$, and concentrated. The residue was purified by chromatography on silica gel using 30% ethyl acetate-hexane to afford 2.13 g (72%) of the title compound as a white solid; $^1$H NMR (CDCl$_3$) δ4.14, 4.34 (dd, AB, 2H, J=12 Hz, C3-H); Mass Spectrum (APCI) m/e 792 (M$^+$NH$_4$).

EXAMPLE 45

4,6,7,15,16-Pentakis(acetyloxy)-3-(2-propenyl)-21, 22-epoxy-18-hydroxy-22-methoxycarbonyl[6α,7α, 15β,16β,21β,22β]D:A-Friedo-A-homo-27,30-dinor-24-oxaoleana-1,20(29)-diene

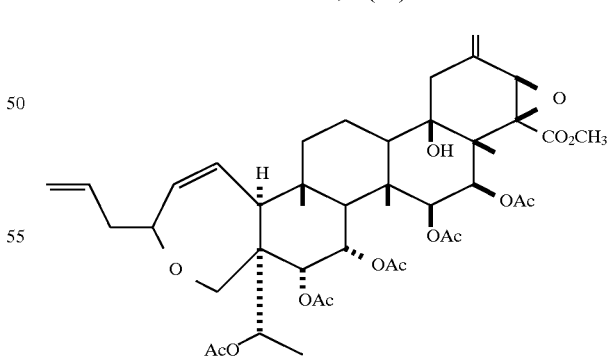

A solution of 1.0 mL of Red-Al [sodium bis(2-methoxyethoxy)aluminum hydride, 65% in toluene] was diluted with 5 mL of dry toluene and cooled to 0° C. under nitrogen. Then 200 μL of ethanol was added and the mixture was stirred at 0° C. for 1 h. A 3.0 mL aliquot of this solution was added th a solution of 500 mg (0.63 mmole) of 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one in 15 mL of dry toluene that had been cooled to 0° C. under nitrogen. After 3 h, the reaction was diluted with 20 mL of dichloromethane and quenched with 20 mL of 1.0M aqueous HCl. The layers were separated and the organic layer was washed with brine and dried over $MgSO_4$. The solvent was concentrated and the residue was dissolved in 10 mL of dry dichloromethane. To 5 mL of this solution was added 0.5 mL (3.14 mmole) of allyltrimethylsilane a the solution was cooled to 0° C. under nitrogen. Then 0.4 mL of boron trifluoride-etherate was added and the solution was stirred at 0° C. After 1 h, the reaction was diluted with 20 mL dichloromethane, washed with saturated aqueous $NaHCO_3$ solution and brine, and dried over $Na_2SO_4$. The solvent was concentrated and the residue was purified by HPLC (Waters RCM, μ Porosil, 25 mm×20 cm) using a mixture of 8:4:1 hexane-methyl tert-butyl ether-acetonitrile:hexane to afford 39 mg (15%) of the 3α-isomer as a white solid; $^1$H NMR ($CDCl_3$) δ3.4, 3.8 (dd, AB, 2H, J=12.1 Hz, C24-C$\underline{H}_2$) 3.9 (s, 3H, $OCH_3$), 5.08 (m, 2H, CH=C$\underline{H}_2$), 5.2 (s, 1H, C29-H), 5.5 (s, 1H, C29-H), 5.8 (m, 1H,$CH_2$C$\underline{H}$=$CH_2$); $^{13}$C NMR ($CDCl_3$) δ116.9, 118.8, 125.7, 131.3, 134.6, 138.5; Mass Spectrum (APCI): m/e 832 ($M^+NH_4$).

Further elution of the column afforded 26 mg (10%) of the 3β-isomer as a white solid; $^1$H NMR ($CDCl_3$) δ3.4, 3.8 (dd, AB, 2H, J=12.2 Hz, C24-C$\underline{H}_2$) 3.9 (s, 3H, $OCH_3$), 5.11 (m, 2H, CH=C$\underline{H}_2$), 5.25 (s, 1H, C29-H), 5.55 (s, 1H, C29-H), 5.84 (m, 1H,$CH_2$C$\underline{H}$=$CH_2$); $^{13}$C NMR ($CDCl_3$) δ117.0, 118.9, 126.1, 131.8, 135.0, 138.2; Mass Spectrum (APCI): m/e 832 ($M^+NH_4$).

EXAMPLE 46

6,7,15,16-Tetrakis(acetyloxy)-21,22-epoxy-4,18-dihydroxy-22-methoxycarbonyl-D:A-Friedo-A-homo-27,30-dinor-24-oxaoleana-1,20(29)-diene

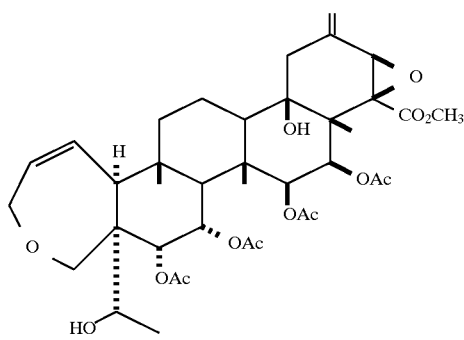

To a solution of 104 mg (0.134 mmole) of 4,6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene in 4.0 mL tetrahydrofuran was added 2.0 mL of a 2.0M aqueous HCL solution. The mixture was heated at 60° C. for 20 h, then was cooled to room temperature and partitioned between dichloromethane and brine. The organic layer was washed with brine, dried over $MgSO_4$, and concentrated. The residue was purified by HPLC (Waters RCM, μ Porosil, 25 mm×10 cm) using a mixture of 9.6:6 (5:4:1 hexane-methyl tert-butyl ether-acetonitrile:hexane) to afford 43 mg (44%) of the title compound as a white solid; $^1$H NMR ($CDCl_3$) δ3.94 (1H, C4-H); Mass Spectrum (APCI): m/e 750 ($M^+NH_4$).

EXAMPLE 47

4-(2-Bromobenzoyl)oxy-6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene

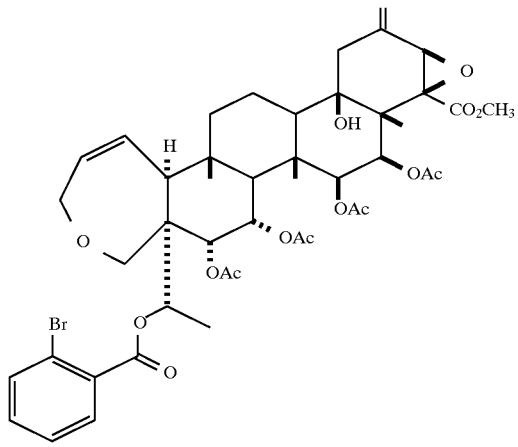

To a solution of 5.9 mg (8.1 μmole) of 6,7,15,16-pentakis(acetyloxy)-21,22-epoxy-4, 18-dihydroxy-22-methoxycarbonyl[6α,7α,15β,16β,21β,22β]D:A-Friedo-A-homo-27,30-dinor-24-oxaoleana-1,20(29)-diene in 0.5 mL pyridine was added 25 uL of 2-bromobenzoyl chloride and 1.2 mg of 4,4-dimethylaminopyridine. The solution was stirred at room temperature for 2 h, then was concentrated and filtered through a pad of silica gel using 2:1 ethyl acetate-hexane. The filtrate was concentrated and the residue was purified by HPLC (Waters RCM, μ Porosil, 10 mm×10 cm) using a mixture of 9.6:6 (5:4:1 hexane-methyl tert-butyl ether-acetonitrile:hexane) to afford 7.0 mg (95%) of the title compound as a white solid; $^1$H NMR ($CDCl_3$) δ5.72 (q, 1H, J=5.5 Hz, C4-H), 7.27–7.35 (m, 2H), 7.71–7.74 (m, 1H), 7.92–7.97 (m, 1H); Mass Spectrum (APCI): m/e 932, 934 ($^{79}$Br-$M^+NH_4$, $^{81}$Br-$M^{+NH}_4$).

Examples 48 through 64 were prepared using the procedures described in Example 47.

EXAMPLE 48

4-(2-Chlorobenzoyl)oxy-6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene

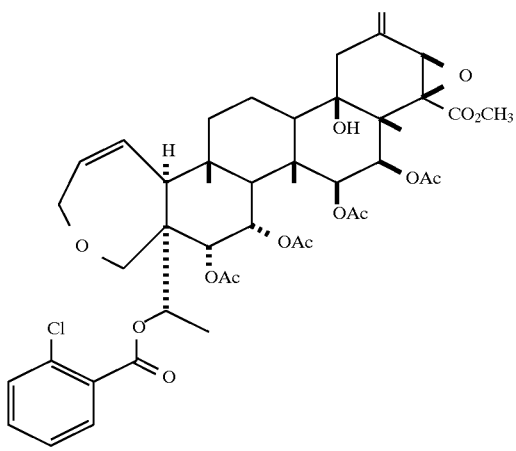

$^1$H NMR (CDCl$_3$) δ5.71 (q, 1H, J=6.5 Hz, C4-H), 7.33(t, 1H, J=7.5 Hz), 7.45(dt, 1H, J=1, 7.5), 7.49 (t, 1H, J=7.5 Hz), 7.96 (dd, 1H, J=1, 7.5 Hz); Mass Spectrum (APCI): m/e 888 (M$^+$NH$_4$).

EXAMPLE 49

4-(2-Iodobenzoyl)oxy-6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene

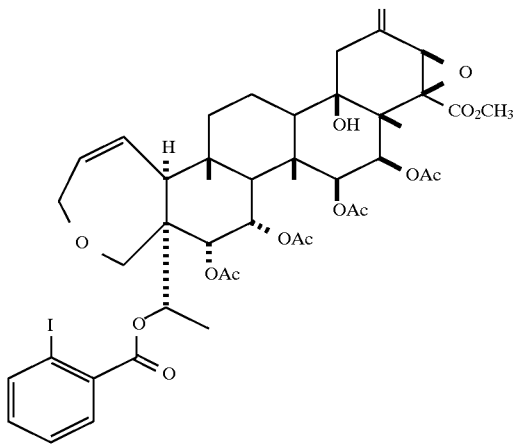

$^1$H NMR (CDCl$_3$) δ5.72 (q, 1H, J=6.5 Hz, C4-H), 7.18 (dt, 1H, J=1.5, 7.5 Hz), 7.42 (dt, 1H, J=1, 7.5), 7.94(d, 1H, J=1.5, 7.5 Hz), 8.06 (dd, 1H, J=1, 7.5 Hz); Mass Spectrum (APCI): m/e 980 (M$^+$NH$_4$).

EXAMPLE 50

4-(2-Methoxybenzoyl)oxy-6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene

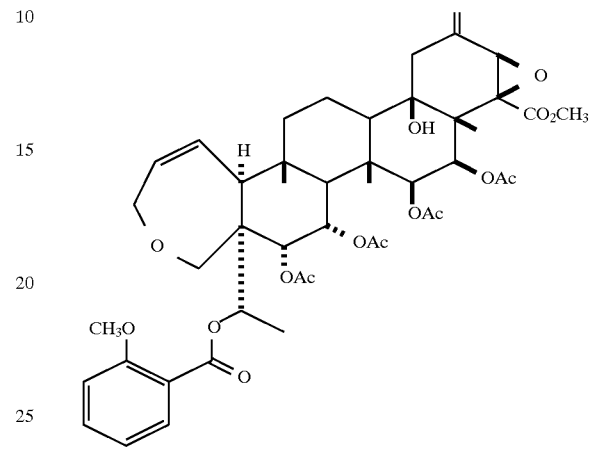

$^1$H NMR (CDCl$_3$) δ3.94 (s, 3H), 5.70 (1H, C4-H), 6.99 (t, 1H, J=7.5 Hz), 7.04 (d, 1H, J=8), 7.53 (ddd, 1H, J=1.5, 7.5, 8 Hz), 7.96 (dd, 1H, J=1.5, 8 Hz); Mass Spectrum (APCI): m/e 884 (M$^+$NH$_4$).

EXAMPLE 51

4-(2-Thienoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

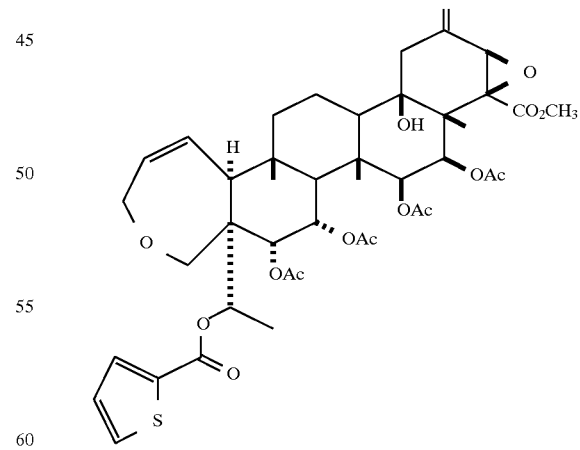

$^1$H NMR (CDCl$_3$) δ$^1$H NMR (CDCl$_3$) δ5.64 (1H, C4-H), 7.14 (m, 1H), 7.59 (m, 1H), 7.82 (m, 1H); Mass Spectrum (APCI): m/e 860 (M$^+$NH$_4$); Mass Spectrum (APCI): m/e 860 (M$^+$NH$_4$).

EXAMPLE 52

4-(3-Bromobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

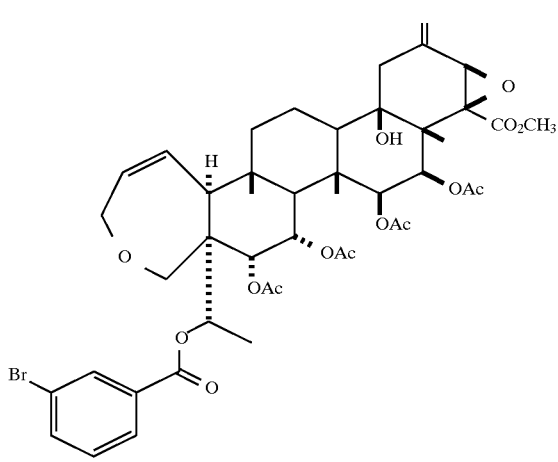

$^1$H NMR (CDCl$_3$) δ5.64 (1H, C4-H), 7.37 (t, 1H, J=7.5 Hz), 7.75 (d, 1H, J=7.5 Hz), 8.01 (d, 1H, J=7.5Hz), 8.25 (s, 1H); Mass Spectrum (APCI): m/e 932, 934 ($^{79}$Br-M$^+$NH$_4$, $^{81}$Br-M$^+$NH$_4$).

EXAMPLE 53

4-(2-Ethoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

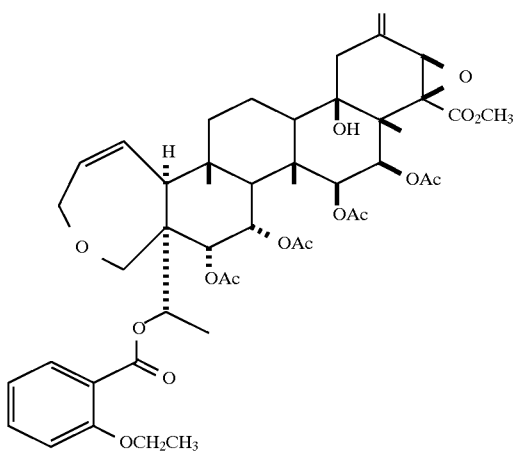

$^1$H NMR (CDCl$_3$) δ1.55 (t, 3H, J=7 Hz), 4.22 (q, 2H, J=7 Hz), 5.66 (q, 1H, J=6.5 Hz, C4-H), 6.97 (t, 1H, J=7.5 Hz), 7.02 (d, 1H, J=8.5 Hz), 7.49 (ddd, 1H, J=1.5, 7.5, 8 Hz), 7.95 (dd, 1H, J=1.5, 7.5 Hz); Mass Spectrum (APCI): m/e 898 (M$^+$NH$_4$).

EXAMPLE 54

4-(4-Phenylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

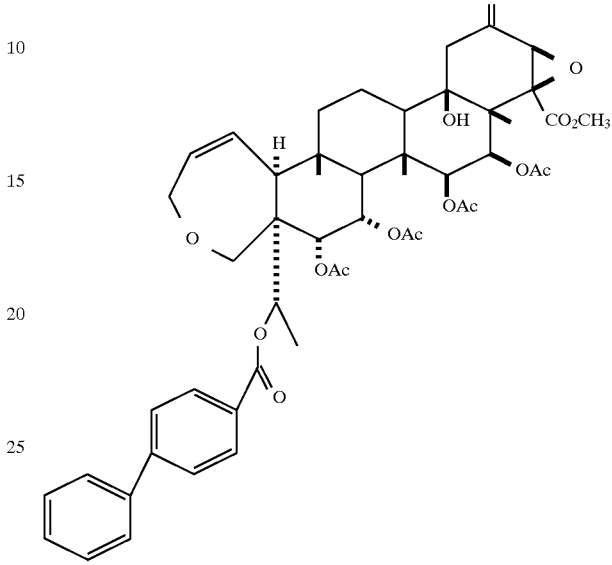

$^1$H NMR (CDCl$_3$) δ5.70 (q, 1H, J=6.5 Hz, C4-H), 7.43 (t, 1H, J=7.5 Hz), 7.50 (t, 2H, J=7.5 Hz), 7.65 (d, 2H, J=7.5 Hz), 7.71 (d, 2H, J=8.25 Hz), 8.15 (d, 2H, J=8.25 Hz); Mass Spectrum (APCI): m/e 930 (M$^+$NH$_4$).

EXAMPLE 55

4-(2-Phenoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

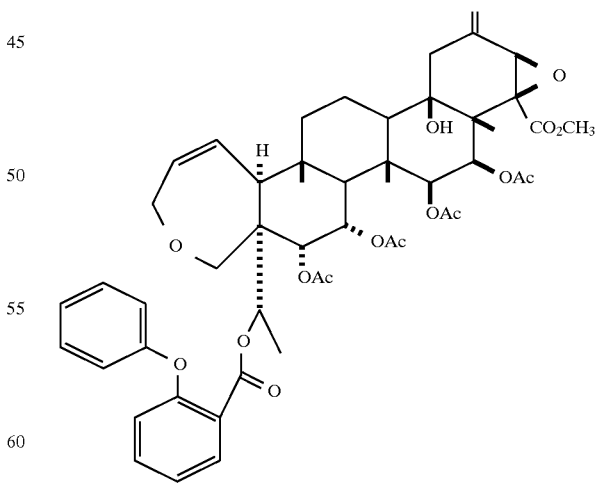

$^1$H NMR (CDCl$_3$) δ5.69 (1H, C4-H), 6.95 (d, 1H, J=7.5 Hz), 7.1–7.2 (m, 2H), 7.36 (t, 2H, J=7 Hz), 7.46 (t, 1H, J=7 Hz), 8.02 (d, 1H, J=7 Hz); Mass Spectrum (APCI): m/e 946 (M$^+$NH$_4$).

EXAMPLE 56

4-(3-Phenoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

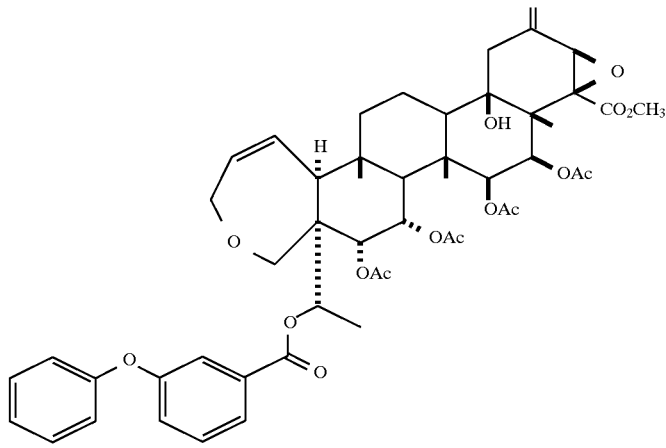

$^1$H NMR (CDCl$_3$) δ5.62 (q, 1H, J=6 Hz, C4-H), 7.06 (d, 2H, J=7.5 Hz), 7.17 (t, 1H, J=7.5 Hz), 7.27–7.31 (m, 1H), 7.39 (t, 2H, J=7.5 Hz), 7.45 (t, 1H, J=7.5 Hz), 7.67 (s, 1H), 7.81 (d, 1H, J=7.5 Hz); Mass Spectrum (APCI): m/e 946 (M$^+$NH$_4$).

EXAMPLE 57

4-(2,4-Difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

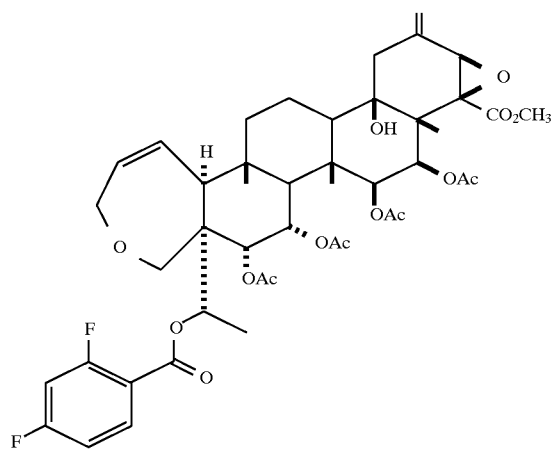

$^1$H NMR (CDCl$_3$) δ5.71 (q, 1H, J=6.5 Hz, C4-H), 6.93–7.0 (m, 2H), 8.0–8.1 (m, 1H); Mass Spectrum (APCI): m/e 890 (M$^+$NH$_4$).

EXAMPLE 58

4-(2,6-Dichlorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

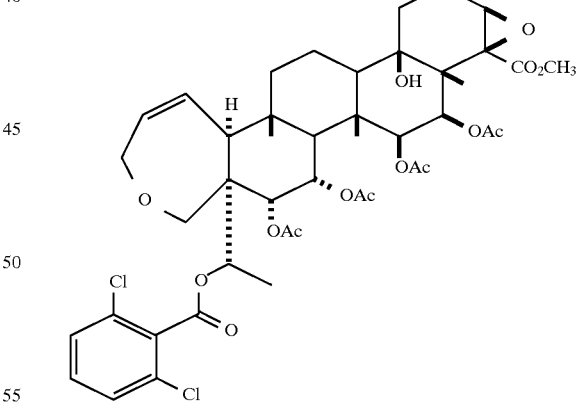

$^1$H NMR (CDCl$_3$) δ5.69 (1H, C4-H), 7.25–7.4 (m, 3H); Mass Spectrum (APCI): m/e 922, 924, 926 ($^{35}$Cl,$^{35}$Cl-M$^+$NH$_4$, $^{35}$Cl,$^{37}$Cl-M$^+$NH$_4$, $^{37}$Cl,$^{37}$Cl-M$^+$NH$_4$).

EXAMPLE 59

4-(2,6-Dimethoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

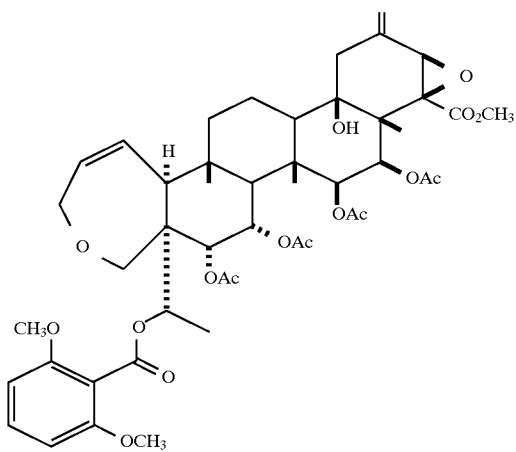

$^1$H NMR (CDCl$_3$) δ3.83 (s, 6H), 5.70 (1H, C4-H), 6.59 (t, 2H, J=8 Hz), 7.31 (t, 1H, J=8 Hz); Mass Spectrum (APCI): m/e 914 (M$^+$NH$_4$).

EXAMPLE 60

4-(2,6-Difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

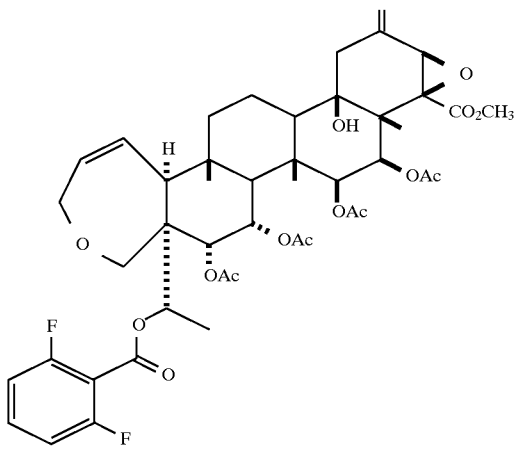

$^1$H NMR (CDCl$_3$) δ$^1$H NMR (CDCl$_3$) δ5.74 (1H, C4-H), 6.97–7.0 (m, 2H), 7.42–7.48 (m, 1H); Mass Spectrum (APCI): m/e 890 (M$^+$NH$_4$).

EXAMPLE 61

4-(2-Acetyloxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

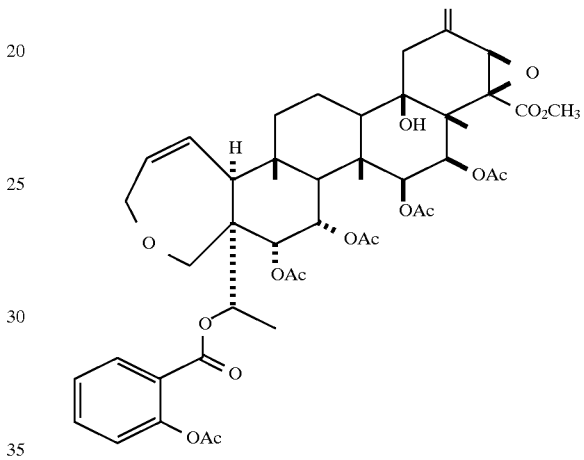

Faster Rotamer: $^1$H NMR (CDCl$_3$) δ1.62 (s, 3H, —OAc), 1.79 (s, 3H, —OAc), 1.84 (s, 3H, —OAc), 1.96 (s, 3H, —OAc), 2.10 (s, 3H, —OAc), 3.60, 3.70 (dd, AB, 2H, J=11.5 Hz, C24-C$\underline{H}_2$), 4.10, 4.33 (dd, AB, 2H, J=17.5 Hz, C3-C$\underline{H}_2$), 5.70 (1H, C4-H), 7.03 (d, 1H, J=8 Hz), 7.21 (t, 1H, J=7.5 Hz), 7.66 (ddd, 1H, J=1.5, 7.5, 8 Hz), 8.17(dd, 1H, J=1.5, 8 Hz); Mass Spectrum (APCI): m/e 898 (M$^+$NH$_4$).

Slower Rotamer: $^1$H NMR (CDCl$_3$) δ1.78 (s, 3H, —OAc), 1.85 (s, 3H, —OAc), 1.88 (s, 3H, —OAc), 1.98 (s, 3H, —OAc), 2.11 (s, 3H, —OAc), 3.42, 3.62 (dd, AB, 2H, J=12 Hz, C24-C$\underline{H}_2$), 4.03, 4.29 (dd, AB, 2H, J=17 Hz, C3-C$\underline{H}_2$), 5.61 (1H, C4-H), 7.01 (d, 1H, J=8 Hz), 7.22 (t, 1H, J=7.5 Hz), 7.64 (ddd, 1H, J=1.5, 7.5, 8 Hz), 8.02 (dd, 1H, J=1,5, 8 Hz); Mass Spectrum (APCI): m/e 898 (M$^+$NH$_4$).

EXAMPLE 62

4-(2-[R]-2-Phenylpropanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

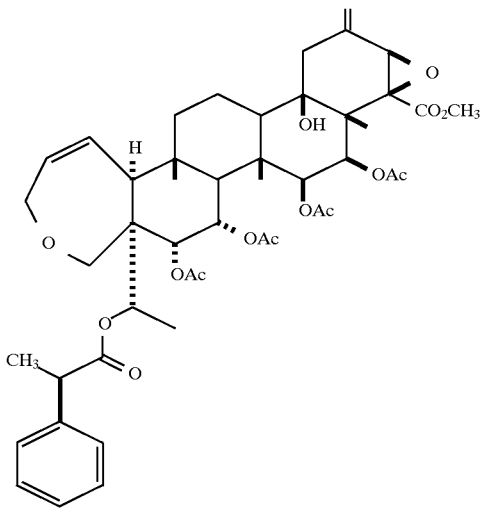

$^1$H NMR (CDCl$_3$) δ1.15 (d, 1H, J=6.5 Hz), 3.70 (q, 1H, J=6.5 Hz), 5.41 (q, 1H, J=6 Hz), C4-H), 7.28–7.40 (m, 5H); Mass Spectrum (APCI): m/e 882 (M$^+$NH$_4$).

EXAMPLE 63

4-(2-[S]-2-Phenylpropanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

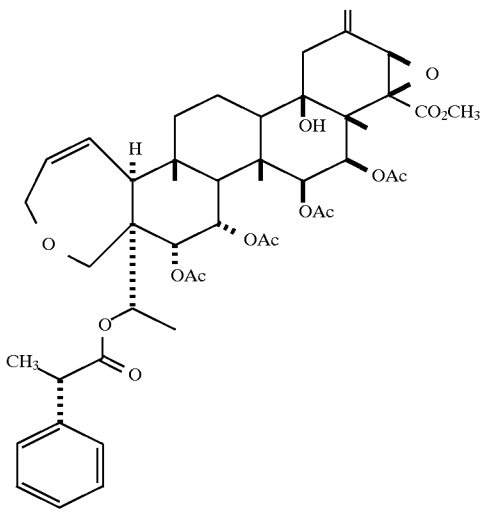

$^1$H NMR (CDCl$_3$) δ0.97 (d, 1H, J=7 Hz), 3.76 (q, 1H, J=7 Hz), 5.33 (q, 1H, J=6.5 Hz), C4-H), 7.28–7.40 (m, 5H); Mass Spectrum (APCI): m/e 882 (M$^+$NH$_4$).

EXAMPLE 64

4-(3,5-Difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene

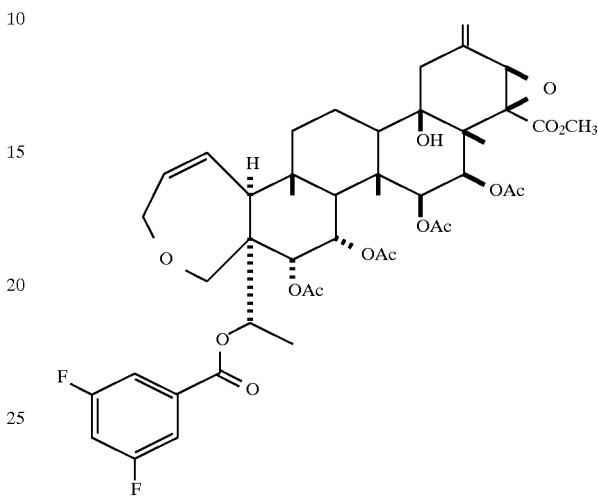

$^1$H NMR (CDCl$_3$) δ5.65 (1H, C4-H), 7.0 (m, 1H), 7.59 (m, 2H); Mass Spectrum (APCI): m/e 890 (M$^+$NH$_4$).

EXAMPLE 65

4,6,7,15,16-Pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one

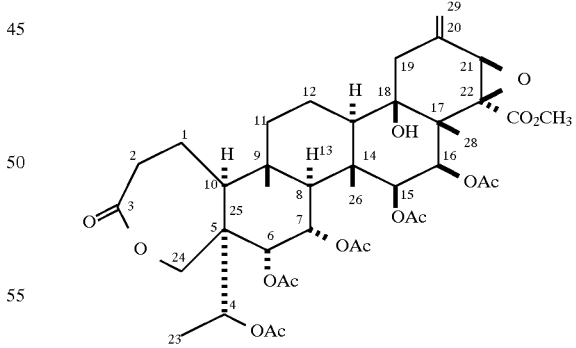

As described in Scheme I, 4,5,6,15,16-pentakis(acetyloxy)-21,22-epoxy-18-hydroxy-22-methoxycarbonyl[6α,7α,15β,16β,21β, 22β]D:A-Friedo-A-homo-27,30-dinor-24-oxaoleana-1,20(29)-diene-3-one, isolated from *Spachea correa* in liquid ammonia with lithium metal will result in the reduction of the C1 olefin group to produce the saturated lactone.

EXAMPLE 66

4,6,7,15,16-Pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-ene

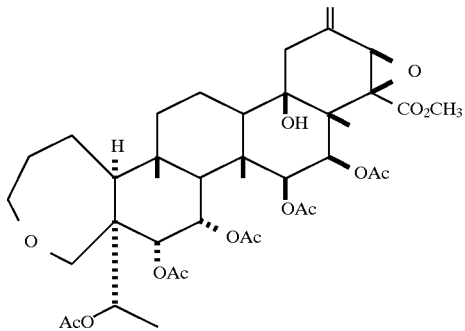

Step A 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-en-3-ol A solution of 3.0 g (3.8 mmole) of 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one in 20 mL of dry dichloromethane is cooled to 0° C. under nitrogen. Then 9 mL of a 1M solution of lithium tri-(tert-butoxy)-aluminum hydride is added dropwise and the solution is stirred at 0° C. After 18 h, the reaction is quenched by dropwise addition of 20 mL of 2M aqueous $H_2SO_4$ and the mixture is diluted with 200 mL of ether. The layers are separated and the aqueous layer is washed with two 100 mL portions of ether. The organic layers are sequentially washed with 20 mL of 2M aqueous $H_2SO_4$ and brine, then combined, dried over $MgSO_4$, and concentrated to afford the title compound, which was used directly in the next step.

Step B 4,6,7,15,16-Pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-ene A sample of crude 4,6,7,15,16-pentakis-(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-ol is dissolved in dry dichloromethane under nitrogen. To this is added triethylsilane, and the solution is stirred at room temperature for 10 min. Then boron trifluoride etherate is added and the mixture is stirred at room temperature for 15 min. The reaction is quenched by addition of saturated aqueous $KHCO_3$ solution and the resulting mixture is partitioned between ether and water. The water layer is washed with ether and the organic extracts are washed with brine, then combined, dried over $MgSO_4$, and concentrated. The residue is purified by chromatography on silica gel using 30% ethyl acetate-hexane to produce the title compound.

EXAMPLE 67A 4,6,7,15,16-Pentakis(acetyloxy)-3-(2-propenyl)-21,22-epoxy-18-hydroxy-22-methoxycarbonyl[6α,7α,15β,16β,21β,22β]D:A-Friedo-A-homo-27,30-dinor-24-oxaoleana-20(29)-ene

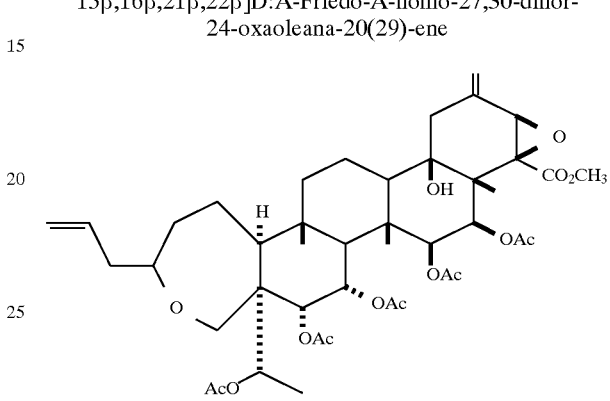

A solution of Red-Al [sodium bis(2-methoxy-ethoxy) aluminum hydride, 65% in toluene] is diluted with dry toluene and cooled to 0° C. under nitrogen. Then ethanol is added and the mixture is stirred at 0° C. for 1 h. A aliquot of this solution is added to a solution of 500 mg (0.63 mmole) of 4,6,7,15,16-pentakis(acetyloxy)-21,22-epoxy-18-hydroxy-22-methoxycarbonyl[6α,7α, 15β,16β,21β,22β]D:A-Friedo-A-homo-27,30-dinor-24-oxaoleana-20(29)-en-3-one in 15 mL of dry toluene that has been cooled to 0° C. under nitrogen. After 3 h, the reaction is diluted with 20 mL of dichloromethane and quenched with 20 mL of 1.0M aqueous HCl. The layers are separated and the organic layer is washed with brine and dried over $MgSO_4$. The solvent is concentrated and the residue is dissolved in 10 mL of dry dichloromethane. To 5 mL of this solution is added 0.5 mL (3.14 mmole) of allyltrimethylsilane and the solution is cooled to 0° C. under nitrogen. Then 0.4 mL of boron trifluoride-etherate is added and the solution is stirred at 0° C. After 1 h, the reaction is diluted with 20 mL dichloromethane, washed with saturated aqueous $NaHCO_3$ solution and brine, and dried over $Na_2SO_4$. The solvent is concentrated and the residue is purified by HPLC (Waters RCM, μ Porosil, 25 mm×20 cm) using a mixture of 8:4:1 hexane-methyl tert-butyl ether-acetonitrile:hexane to produce the 3α-isomer. Further elution of the column affords the 3β-isomer.

EXAMPLE 68

6,7,15,16-Tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-en-3-one

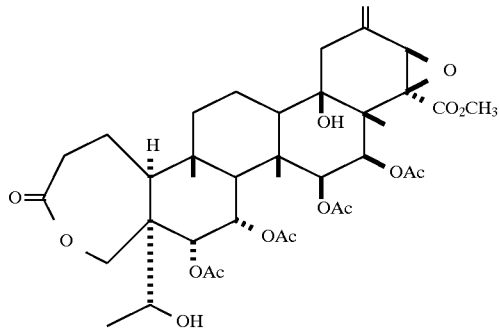

A solution of 102.1 mg (0.130 mmole) of 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one in 4 mL of tetrahydrofuran and 2 mL of 3M aqueous HCl is heated at 40° C. for 24 h. The solution is diluted with dichloromethane and the layers were separated. The organic layer is washed with 0.1M phosphate buffer (pH 7), then dried over MgSO$_4$ and concentrated. The residue is purified by silica gel chromatography with 2:1 ethyl acetate-hexane to provide the title compound.

EXAMPLE 69

6,7,15,16-Tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-ene

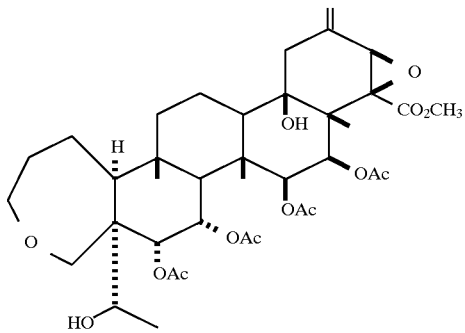

To a solution of 4,6,7,15,16-pentaakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-ene in 4.0 mL tetrahydrofuran is added 2.0 mL of a 2.0M aqueous HCL solution. The mixture is heated at 60° C. for 20 h, then is cooled to room temperature and partitioned between dichloromethane and brine. The organic layer is washed with brine, dried over MgSO$_4$, and concentrated. The residue is purified by HPLC (Waters RCM, μ Porosil, 25 mm×10 cm) using a mixture of 9.6:6 (5:4:1 hexane-methyl tert-butyl ether-acetonitrile:hexane) to produce the title compound.

EXAMPLE 70

4-Benzoyloxy-6,7,15,16-Tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one

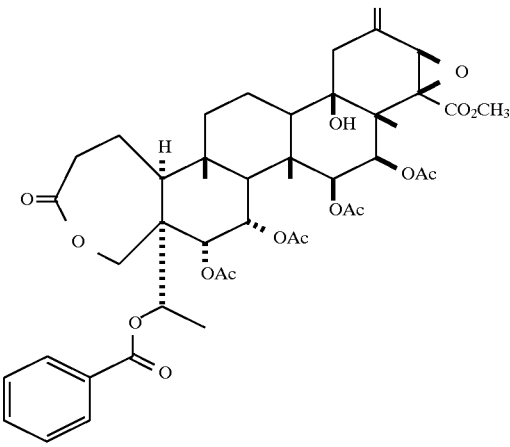

To a solution of 17.5 mg (23.5 μmole) of 6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-en-3-one in 0.5 mL pyridine is added 27.5 mL (237 μmole) of benzoyl chloride. The solution is stirred at room temperature for 4 h, then concentrated under reduced pressure. The residue is first filtered through a plug of silica gel and then purified by HPLC (Waters RCM, μ Porosil, 10 mm×10 cm) using a mixture of 9.6:6 (5:4:1 hexane-methyl tert-butyl ether-acetonitrile:hexane) to produce the title compound.

EXAMPLE 71

4-(1-Imidazolylcarbonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one

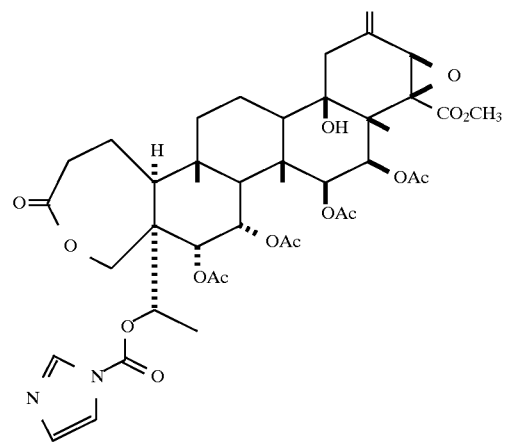

A solution of 25.2 mg (34 μmole) of 6,7,15,16-tetrakis (acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-en-3-one and 27.4 mg (0.169 mmole) of carbonyl diimidazole in 2 mL of benzene are heated at 70° C. After 24 h, the solution is filtered through a pad of silica gel using 2:1 ethyl acetate-hexane and the filtrate is concentrated. The residue is purified by HPLC (Waters RCM, μ Porosil, 10 mm×10 cm) using a mixture 5:4:1 hexane-methyl tert-butyl ether-acetonitrile to afford the title compound.

Following the procedures described above Examples 72 and 73 are prepared.

EXAMPLE 72

4-(N-Phenylmethylcarbamoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one

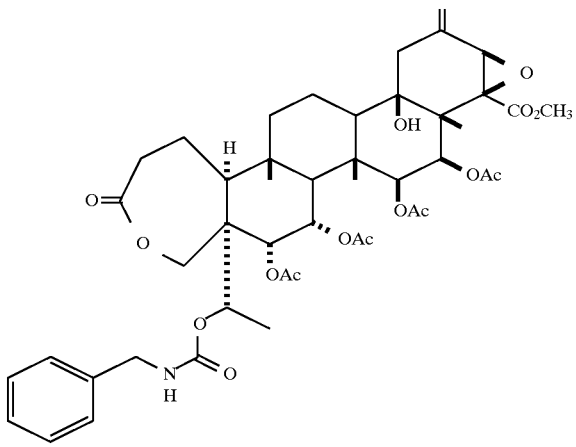

EXAMPLE 73

4-(N-Butylcarbamoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one

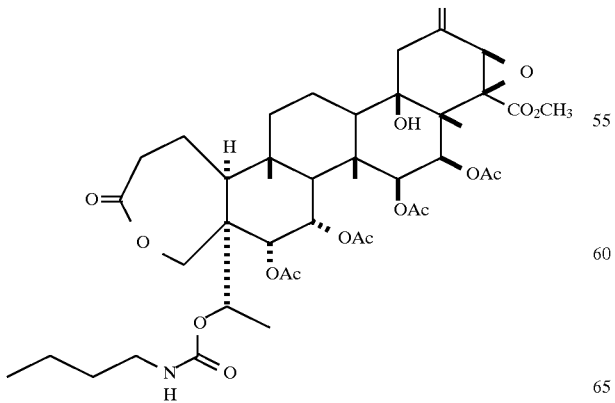

What is claimed is:

1. A compound of structural Formula I:

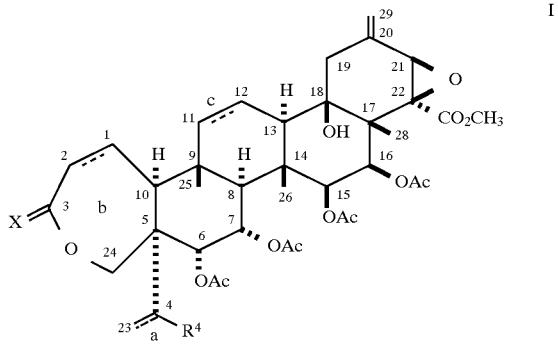

or a pharmaceutically acceptable salt, crystal form or hydrate, wherein:

X is: O, S, NH or H and $R^1$;

a is: a single bond, or a double bond when $R^4$ is absent;

b and c are independently: a single bond, or a double bond;

n is: 1 to 4;

m is: 1 to 4;

r is: 0 or 1;

s is: 0 or 1;

$R^1$ and $R^2$ are independently:
  a) H, or
  b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
  a) $—(C_1-C_6)$-alkyl, alkyl as defined above;
  b) $—(C_1-C_6)$-alkenyl, wherein alkenyl is unsubstituted or substituted with one, two or three substituents selected from from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above;

c) —($C_1$–$C_6$)-alkynyl, wherein alkynyl is unsubstituted or substituted with one, two or three substituents selected from the group consisting of: Br, Cl, F, I, ($C_1$–$C_6$)-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above, d) -aryl, aryl as defined above, or e) -heteroaryl, heteroaryl as defined above;

$R^4$ is:

a) absent and a is a double bond;

b) —H, c) —OH, d) =O, e) —O[(C=O)$O_r$]$_s$$C_1$–$C_{10}$-alkyl, alkyl as defined above, f) —O[(C=O)$O_r$]$_s$$C_2$–$C_{10}$-alkenyl, as defined above, g) —O[(C=O)$O_r$]$_s$$C_2$–$C_6$-alkynyl, alkynyl as defined above, h) —O[(C=O)$O_r$]$_s$($C_3$–$C_7$)-cycloalkyl, i) —O[(C=O)$O_r$]$_s$aryl, aryl as defined above, j) —O[(C=O)$O_r$]$_s$heteroaryl, heteroaryl as defined above, k) —O($CH_2$)$_n$O($CH_2$)$_m$heteroaryl, heteroaryl as defined above, l) —O($CH_2$)$_n$O($CH_2$)$_m$aryl, aryl as defined above, m) —OC(=O)$NR^1R^2$, n) —$OSO_2R^3$, o) —$NR^1R^2$, or p) ($C_2$–$C_6$)-alkenyl, alkenyl as described above.

2. The compound of structural Formula I, as recited in claim 1,

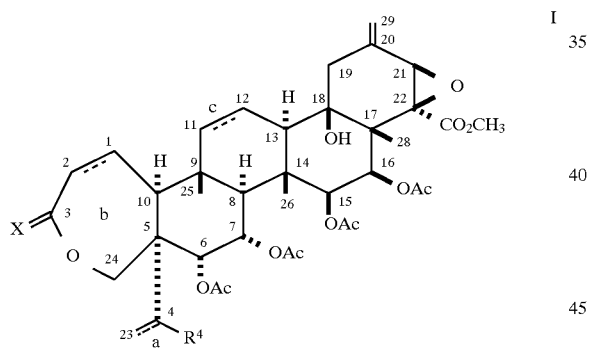

or a pharmaceutically acceptable salt, crystal form or hydrate, wherein:

X is: O, S, or NH;

a is: a single bond;

b and c are independently: a single bond or a double bond;

n is: 1 to 4;

m is: 1 to 4;

r is: 0 or 1;

s is: 0 or 1;

$R^1$ and $R^2$ are independently:

a) H, or b) ($C_1$–$C_6$)-alkyl, wherein alkyl is unsubstituted or substituted with one, two or three substituents selected from the group consisting of: Br, Cl, F, I, ($C_1$–$C_6$)-alkoxy, vinyl, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl, wherein aryl is defined as phenyl or naphthyl, unsubstituted or substituted with one, two or three substituents selected from the group consisting of: Br, Cl, F, I, ($C_1$–$C_6$)-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:

a) —($C_1$–$C_6$)-alkyl, alkyl as defined above;

b) —($C_1$–$C_6$)-alkenyl, wherein alkenyl is unsubstituted or substituted with one, two or three substituents selected from from the group consisting of: Br, Cl, F, I, ($C_1$–$C_6$)-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above;

c) —($C_1$–$C_6$)-alkynyl, wherein alkynyl is unsubstituted or substituted with one, two or three substituents selected from the group consisting of: Br, Cl, F, I, ($C_1$–$C_6$)-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above, d) -aryl, aryl as defined above, or e) -heteroaryl, heteroaryl as defined above;

$R^4$ is:

a) absent and a is a double bond;

b) —H, c) —OH, d) =O, e) —O[(C=O)$O_r$]$_s$$C_1$–$C_{10}$-alkyl, alkyl as defined above, f) —O[(C=O)$O_r$]$_s$$C_2$–$C_{10}$-alkenyl, as defined above, g) —O[(C=O)$O_r$]$_s$$C_2$–$C_6$-alkynyl, alkynyl as defined above, h) —O[(C=O)$O_r$]$_s$($C_3$–$C_7$)-cycloalkyl, i) —O[(C=O)$O_r$]$_s$aryl, aryl as defined above, j) —O[(C=O)$O_r$]$_s$heteroaryl, heteroaryl as defined above, k) —O($CH_2$)$_n$O($CH_2$)$_m$heteroaryl, heteroaryl as defined above, l) —O($CH_2$)$_n$O($CH_2$)$_m$aryl, aryl as defined above, m) —OC(=O)$NR^1R^2$, n) —$OSO_2R^3$, o) —$NR^1R^2$ or p) ($C_2$–$C_6$)-alkenyl, alkenyl as described above.

3. The compound of structural Formula I, as recited in claim 2,

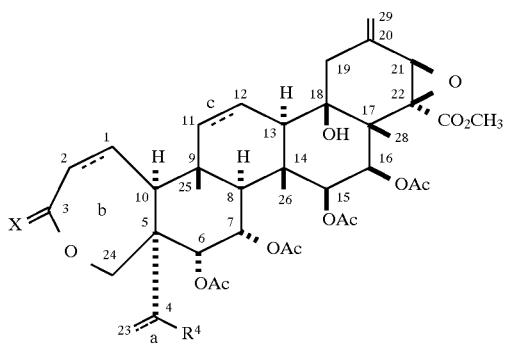

or a pharmaceutically acceptable salt, crystal form or hydrate, wherein:

X is: O;

a is: a single bond;

b and c are independently: a single bond or a double bond;

n is: 1 to 4;

m is: 1 to 4;

r is: 0 or 1;

s is: 0 or 1;

$R^1$ and $R^2$ are independently a) H, or b) ($C_1$–$C_6$)-alkyl, wherein alkyl is unsubstituted or substituted with one, two or three substituents selected from the group consisting of: Br, Cl, F, I, ($C_1$–$C_6$)-alkoxy, vinyl, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl, wherein aryl is defined as phenyl or naphthyl, unsubstituted or substituted with one, two or three substituents selected from the group consisting of: Br, Cl, F, I, ($C_1$–$C_6$)-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:

a) —($C_1$–$C_6$)-alkyl, alkyl as defined above, b) -aryl, aryl as defined above, or c) -heteroaryl, heteroaryl as defined above;

$R^4$ is:

a) —O[(C=O)$O_r$]$_s C_1$–$C_{10}$-alkyl, alkyl as defined above, b) —O[(C=O)$O_r$]$_s$($C_3$–$C_7$)-cycloalkyl, c) —O[(C=O)$O_r$]$_s$aryl, aryl as defined above, d) —O[(C=O)$O_r$]$_s$heteroaryl, heteroaryl as defined above, e) —O($CH_2$)$_n$O($CH_2$)$_m$heteroaryl, heteroaryl as defined above, f) —O($CH_2$)$_n$O($CH_2$)$_m$aryl, aryl as defined above, g) —OC(=O)$NR^1 R^2$, or h) —O$SO_2R^3$.

4. The compound of structural Formula I, as recited in claim 3, or a pharmaceutically acceptable salt, crystal form or hydrate, wherein $R^4$ is:

a) —O[(C=O)$O_r$]$_s$aryl, wherein aryl is defined as phenyl or naphthyl, unsubstituted or substituted with one, two or three substituents selected from the group consisting of: Br, Cl, F, I, ($C_1$–$C_6$)-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, or b) —O[(C=O)$O_r$]$_s$heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring.

5. The compound of structural Formula I, as recited in claim 1,

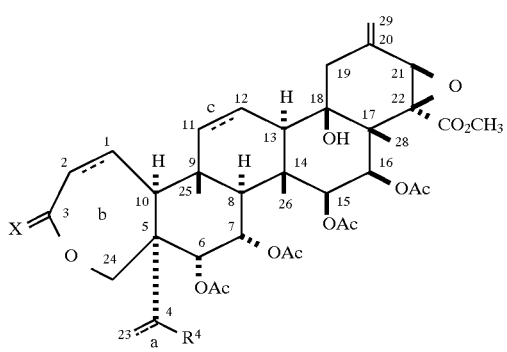

or a pharmaceutically acceptable salt, crystal form or hydrate, wherein:

X is: H and $R^1$;

a is: a single bond;

b and c are independently: a single bond or a double bond;

n is: 1 to 4;

m is: 1 to 4;

r is: 0 or 1;

s is: 0 or 1;

$R^1$ and $R^2$ are independently:

a) H, or b) ($C_1$–$C_6$)-alkyl, wherein alkyl is unsubstituted or substituted with one, two or three substituents selected from the group consisting of: Br, Cl, F, I, ($C_1$–$C_6$)-alkoxy, vinyl, cyano, oxo, nitro, hydroxy, CHO, $CO_2H$, $COC_1$–$C_6$-alkyl, $CO_2C_1$–$C_6$-alkyl,

81

$CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —$(C_1-C_6)$-alkyl, alkyl as defined above;
b) —$(C_1-C_6)$-alkenyl, wherein alkenyl is unsubstituted or substituted with one, two or three substituents selected from from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above;
c) —$(C_1-C_6)$-alkynyl, wherein alkynyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above,
d) -aryl, aryl as defined above, or
e) -heteroaryl, heteroaryl as defined above;

$R^4$ is:
a) absent and a is a double bond;
b) —H,
c) —OH,
d) =O,
e) —O[(C=O)O$_r$]$_s$C$_1$–C$_{10}$-alkyl, alkyl as defined above,
f) —O[(C=O)O$_r$]$_s$C$_2$–C$_{10}$-alkenyl, as defined above,
g) —O[(C=O)O$_r$]$_s$C$_2$–C$_6$-alkynyl, alkynyl as defined above,
h) —O[(C=O)O$_r$]$_s$(C$_3$–C$_7$)-cycloalkyl,
i) —O[(C=O)O$_r$]$_s$aryl, aryl as defined above,
j) —O[(C=O)O$_r$]$_s$heteroaryl, heteroaryl as defined above,
k) —O(CH$_2$)$_n$O(CH$_2$)$_m$heteroaryl, heteroaryl as defined above,
l) —O(CH$_2$)$_n$O(CH$_2$)$_m$aryl, aryl as defined above,
m) —OC(=O)NR$^1$R$^2$,
n) —OSO$_2$R$^3$, or
o) —NR$^1$R$^2$.

6. The compound of structural Formula I, as recited in claim 5,

82

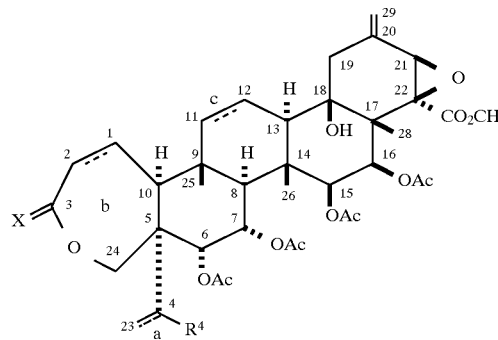

or a pharmaceutically acceptable salt, crystal form or hydrate, wherein:

X is: H and $R^1$;
a is: a single bond;
b and c are independently: a single bond or a double bond;
n is: 1 to 4;
m is: 1 to 4;
r is: 0 or 1;
s is: 0 or 1;
$R^1$ and $R^2$ are independently:
a) H, or
b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —$(C_1-C_6)$-alkyl, alkyl as defined above;
b) —$(C_1-C_6)$-alkenyl, wherein alkenyl is unsubstituted or substituted with one, two or three substituents selected from from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above;
c) —$(C_1-C_6)$-alkynyl, wherein alkynyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above, d) -aryl, aryl as defined above, or
e) -heteroaryl, heteroaryl as defined above;

$R^4$ is:
a) —OH,
b) —O[(C=O)O$_r$]$_s$C$_1$–C$_{10}$-alkyl, alkyl as defined above,
c) —O[(C=O)O$_r$]$_s$(C$_3$–C$_7$)-cycloalkyl,
d) —O[(C=O)O$_r$]$_s$aryl, aryl as defined above,
e) —O[(C=O)O$_r$]$_s$heteroaryl, heteroaryl as defined above,
f) —O(CH$_2$)$_n$O(CH$_2$)$_m$heteroaryl, heteroaryl as defined above,
g) —O(CH$_2$)$_n$O(CH$_2$)$_m$aryl, aryl as defined above,
h) —OC(=O)NR$^1$ R$^2$, or
i) —OSO$_2$R$^3$.

7. A compound selected from the group consisting of:

6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-dien-3-one;

4-benzoyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-chlorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-methoxyacetyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-chloroacetyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-bromobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-cyanobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(propanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2,2-dimethylpropanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(cyclohexylcarbonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-nitrobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(3-methylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(4-methoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-bromobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2,3-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(3-methoxybenzoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(1-naphthoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-naphthoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-iodobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-trifluoromethylbenzoyl)oxy-6,7,15,16-tetrakis(acetyloxy)-21,22-epoxy-18-hydroxy-22-methoxycarbonyl [6α,7α,15β,16β,21β,22β]D:A-Friedo-A-homo-27,30-dinor-24-oxaoleana-1,20(29)-dien-3-one;

4-(pentanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-fluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(2-furoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(benzyloxycarbonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-(benzyloxymethyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;

4-methanesulfonyloxy-6,7,15,16-tetrakis(acetyloxy)-21,22-epoxy-18-hydroxy-22-methoxycarbonyl[6α,7α,15β,16β, 21β,22β]D:A-Friedo-A-homo-27,30-dinor-24-oxaoleana-1,20(29)-dien-3-one;
4-(4-methylbenzenesulfonyl)oxy-6,7,15,16-tetrakis(acetyloxy)-21,22-epoxy-18hydroxy-22-methoxycarbonyl[6α,7α,15β,16β,21β,22β]D:A-Friedo-A-homo-27,30-dinor-24-oxaoleana-1,20(29)-dien-3-one;
4-(phenylmethanesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-(4-chlorobenzenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-(4-methoxybenzenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-butanesulfonyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-(2-nitrobenzenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-(2-thiophenesulfonyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-(1-imidazolylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-(N-phenylmethylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4-(N-butylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one;
4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4,6,7,15,16-pentakis(acetyloxy)-3-(2-propenyl)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;
4-(2-bromobenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;
4-(2-chlorobenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;
4-(2-iodobenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;
4-(2-methoxybenzoyl)oxy-6,7,15,16-pentakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-1,20(29)-diene;
4-(2-thienoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(3-bromobenzoyl)oxy-6,7,15,16-tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2-ethoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(4-phenylbenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2-phenoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(3-phenoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2,4-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2,6-dichlorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2,6-dimethoxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2,6-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2-acetyloxybenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2-[R]-2-phenylpropanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(2-[S]-2-phenylpropanoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4-(3,5-difluorobenzoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-diene;
4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;
4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-ene;
4,6,7,15,16-pentakis(acetyloxy)-3-(2-propenyl)-21,22-epoxy-18-hydroxy-22-methoxycarbonyl[3α,6α,7α,15β, 16β,21β,22β]D:A-Friedo-A-homo-27,30-dinor-24-oxaoleana-20(29)-ene;

4,6,7,15,16-pentakis(acetyloxy)-3-(2-propenyl)-21,22-epoxy-18-hydroxy-22-methoxycarbonyl[3α,6α,7α,15β,16β,21β,22β]D:A-Friedo-A-homo-27,30-dinor-24-oxaoleana-20(29)-ene;

6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-en-3-one;

6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-ene;

4-benzoyloxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;

4-(1-imidazolylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;

4-(N-phenylmethylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one;

4-(N-butylcarbamoyl)oxy-6,7,15,16-tetrakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one.

8. A method treating a condition in a mammal, the treatment of which is effected or facilitated by $K_v1.3$ inhibition, comprising the administration, in an amount that is effective at inhibiting $K_v3$, of a compound of Formula I.

9. The method as recited in claim 8, wherein the condition is an autoimmune disease.

10. A method of preventing or treating the resistance to transplantation or transplantation rejection of organs or tissues into a patient in need thereof, which comprises the administration of a compound of claim 1.

11. A method of suppressing the immune system in a subject in need thereof, which comprises the administration to the subject of an immune suppressing amount of a compound of Formula I, as recited in claim 1.

12. A pharmaceutical formulation comprising a pharmaceutically acceptable carrier and a therapeutically effective amount of the compound of Formula I, as recited in claim 1 or a pharmaceutically acceptable crystal form or hydrate thereof.

13. The pharmaceutical formulation of claim 12, comprising in addition, an immunosuppressive agent comprising azathioprine, brequinar sodium, deoxyspergualin, mizaribine, mycophenolic acid morpholino ester, cyclosporin, FK-506 and rapamycin.

14. The method of claim 11, comprising the coadministration with a second immunosuppressive agent.

15. A method of treating a condition in a mammal, the treatment of which is effected or facilitated by $K_v1.3$ inhibition, comprising the coadministration of a therapeutically effective amount of a compound of Formula I, as recited in claim 1, with a second immunosuppressive agent.

* * * * *